US010758631B2

(12) United States Patent
Elitzin et al.

(10) Patent No.: US 10,758,631 B2
(45) Date of Patent: Sep. 1, 2020

(54) SOLID CYANINE DYES

(71) Applicant: LI-COR, Inc., Lincoln, NE (US)

(72) Inventors: Vassil Elitzin, Lincoln, NE (US); William M. Volcheck, Lincoln, NE (US); Katie Schaepe, Lincoln, NE (US); Rahul Patil, Lincoln, NE (US)

(73) Assignee: LI-COR, INC., Lincoln, NE (US)

( * ) Notice: Subject to any disclaimer, the term of this patent is extended or adjusted under 35 U.S.C. 154(b) by 26 days.

(21) Appl. No.: 15/951,911

(22) Filed: Apr. 12, 2018

(65) Prior Publication Data

US 2018/0296704 A1 Oct. 18, 2018

Related U.S. Application Data

(63) Continuation of application No. PCT/US2018/026882, filed on Apr. 10, 2018.

(60) Provisional application No. 62/484,242, filed on Apr. 11, 2017.

(51) Int. Cl.
*A61K 49/00* (2006.01)
*C09B 23/01* (2006.01)
*A61M 5/00* (2006.01)
*C09B 23/08* (2006.01)
*A61B 5/20* (2006.01)
*A61B 5/00* (2006.01)

(52) U.S. Cl.
CPC ...... *A61K 49/0032* (2013.01); *A61K 49/0063* (2013.01); *A61M 5/007* (2013.01); *C09B 23/0025* (2013.01); *C09B 23/0066* (2013.01); *C09B 23/0075* (2013.01); *C09B 23/086* (2013.01); *A61B 5/0071* (2013.01); *A61B 5/201* (2013.01); *A61B 2505/05* (2013.01)

(58) Field of Classification Search
CPC .. A61K 9/00; A61K 49/0032; A61K 49/0063; A61K 49/00; A61M 5/007; C09B 23/0075; C09B 23/0025; C09B 23/0066; C09B 23/086; A61B 2505/05; A61B 5/201; A61B 5/0071
USPC .... 424/1.11, 1.65, 1.81, 1.85, 1.89, 9.1, 9.2, 424/9.6, 1.73
See application file for complete search history.

(56) References Cited

U.S. PATENT DOCUMENTS

| | | | | |
|---|---|---|---|---|
| 7,488,468 B1 * | 2/2009 | Miwa | ............... | A61K 49/0032 424/9.6 |
| 7,597,878 B2 * | 10/2009 | Kovar | ............... | A61K 49/0032 424/1.11 |
| 7,993,927 B2 * | 8/2011 | Frangioni | ............... | B82Y 15/00 435/40.5 |
| 10,100,198 B2 * | 10/2018 | Kundu | ............... | G01N 33/582 |
| 2008/0154102 A1 * | 6/2008 | Frangioni | ............ | A61B 5/0059 600/317 |
| 2016/0144058 A1 | 5/2016 | Draney et al. | | |

FOREIGN PATENT DOCUMENTS

| | | |
|---|---|---|
| EP | 753584 | 1/1997 |
| JP | 06145539 | 5/1994 |
| WO | 0016810 | 3/2000 |
| WO | 2008076467 | 6/2008 |
| WO | 2010091243 | 8/2010 |
| WO | 2016085884 | 6/2016 |

OTHER PUBLICATIONS

Akers et al., "Predicting in Vivo Fluorescence Lifetime Behavior of Near-infrared Fluorescent Contrast Agents using in Vitro Measurements", Journal of Biomedical Optics, vol. 13, No. 5, Sep.-Oct. 2008, pp. 054042-1-054042-9.
Goiffon et al., "Dynamic Noninvasive Monitoring of Renal Function in Vivo by Fluorescence Lifetime Imaging", Journal of Biomedical Optics, vol. 14, No. 2, Mar. 2009, 3 pages.
Sato et al., "Role of Fluorophore Charge on the In Vivo Optical Imaging Properties of Near-Infrared Cyanine Dye/Monoclonal Antibody Conjugates", Bioconjugate Chemistry, ACS Publications, Oct. 2015, pp. 1-48
Schols et al., "Application of a New Dye for Near-Infrared Fluorescence Laparoscopy of the Ureters: Demonstration in a Pig Model", Diseases of the Colon & Rectum, vol. 57, Mar. 2014, pp. 407-411.
Schols , "Near-Infrared Fluorescence Laparoscopy of the Cystic Duct and Artery in Pigs: Performance of a Preclinical Dye", Journal of Laparoendoscopic & Advanced Surgical Techniques, vol. 24, No. 5, Nov. 2014, pp. 318-323.
Tanaka et al., "Real-Time Intraoperative Ureteral Guidance Using Invisible Near-Infrared Fluorescence", Journal of Urology, vol. 178, No. 5, Nov. 2007, pp. 2197-2202.
Zaheer et al., "IRDYE78 Conjugates for near-infrared Fluorescence Imaging", Molecular Imaging, vol. 1, No. 4, Oct. 1, 2002, pp. 354-364.

(Continued)

*Primary Examiner* — D. L. Jones
(74) *Attorney, Agent, or Firm* — Kilpatrick Townsend & Stockton LLP

(57) ABSTRACT

Polymorphs of Formula I, which is 2-((E)-2-((E)-3-(2-((E)-3,3-dimethyl-5-sulfonato-1-(4-sulfonatobutyl)indolin-2-ylidene)ethylidene)-2-phenoxycyclohex-1-en-1-yl)vinyl)-3,3-dimethyl-1-(4-sulfonatobutyl)-3H-indol-1-ium-5-sulfonate and methods of making are provided.
A method for organ imaging, comprising administering to a subject, a diagnostic effective amount of a composition comprising a polymorph of Formula I are also provided. In one embodiment, the organ includes one or more of kidney, bladder, ureter, urethra, bile ducts, liver, and gall bladder.

17 Claims, 11 Drawing Sheets

(56) References Cited

OTHER PUBLICATIONS

Caira, "Crystalline Polymorphism of Organic Compounds," Topics in Current Chemistry, Springer, vol. 198, Jan. 1, 1998, pp. 163-208.
PCT/US2018/026882, "International Search Report and Written Opinion," dated Aug. 31, 2018, 20 pages.
Bilimoria et al., "Laparoscopic-assisted vs. open colectomy for cancer: comparison of short-term outcomes from 121 hospitals," J Gastrointest Surg, (2008), vol. 12, No. 11, pp. 2001-2009.
Kobayashi et al., "Total laparoscopic hysterectomy in 1253 patients using an early ureteral identification technique," J Obstet Gynaecol Res, (2012), vol. 38, No. 9, pp. 1194-1200.
Park et al., "Ureteral injury in gynecologic surgery: a 5-year review in a community hospital," Korean J. Urol., (2012), vol. 53, No. 2, pp. 120-125.
Simorov et al., "Laparoscopic colon resection trends in utilization and rate of conversion to open procedure: a national database review of academic medical centers," Ann Surg., (2012), vol. 256, No. 3, pp. 462-468.
U.S. Appl. No. 16/687,450, filed Nov. 18, 2019.
U.S. Appl. No. 16/687,479, filed Nov. 18, 2019.

\* cited by examiner

SOLID CYANINE DYES

CROSS-REFERENCES TO RELATED APPLICATIONS

This application is a Continuation of PCT/US2018/026882 filed Apr. 10, 2018, which claims priority to U.S. Provisional Patent Application No. 62/484,242 filed Apr. 11, 2017, the disclosures which are hereby incorporated by reference in their entirety for all purposes.

BACKGROUND

Fluorescence imaging using cyanine dyes is a rapidly emerging field to support surgical navigation and provide real-time illumination of anatomic structures. Emissions in the 700-900 nm range may avoid interference from tissue auto-fluorescence and can penetrate approximately 1 cm of tissue, as described in Adams et al., "Comparison of visible and near-infrared wavelength-excitable fluorescent dyes for molecular imaging of cancer" *J Biomed Opt.* 2007 12(2), 024017; and, Keereweer et al., "Optical Image-Guided Cancer Surgery: Challenges and Limitations" *Clin Cancer Res.* 2013 19(14), 3745-3754.

Another application of fluorescence imaging is for the real-time intra-operative imaging of the biliary anatomy, including the biliary duct and cystic duct. Current methods often use indocyanine green (ICG) dye by either intra-biliary injection or intravenous injection before surgery. However, studies have shown clear problems in using ICG dye. These include poor efficiency and kinetics of excretion into bile (Tanaka et al., "Real-time intraoperative assessment of the extrahepatic bile ducts in rats and pigs using invisible near-infrared fluorescent light" *Surgery* 2008 144(1) 39-48) and adverse reaction with the patient (Benya et al., "Adverse reactions to indocyanine green: a case report and a review of the literature" *Cathet Cardiovasc Diagn.* 1989 17(4) 231-233).

There exists a need for sensitive compositions and methods to detect and measure an internal target non-invasively. Specifically, there exists a need for improved, stable cyanine dyes to detect injuries to various organs that may occur during laparoscopic or robotic surgery. The present invention satisfies these and other needs.

BRIEF SUMMARY

In one embodiment, the present disclosure provides a solid form, which solid form is Form A-1 to A-13 of Formula I:

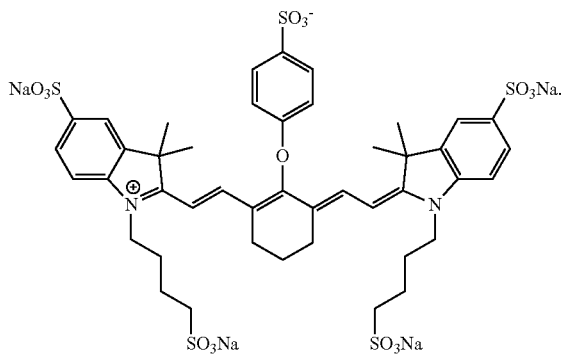

(I)

In certain aspects, the solid form of Formula I is Form A-1 having an X-ray powder diffraction pattern shown in FIG. 1A, with the peaks tabulated in Table 1A.

In certain aspects, the solid form of Formula I is Form A-1 having an X-ray powder diffraction pattern shown in FIG. 1B, with the peaks tabulated in Table 1B.

In certain aspects, the solid form of Formula I is Form A-2 having an X-ray powder diffraction pattern shown in FIG. 2, with the peaks tabulated in Table 2.

In certain aspects, the solid form of Formula I is Form A-3 having an X-ray powder diffraction pattern shown in FIG. 3, with the peaks tabulated in Table 3.

In certain aspects, the solid form of Formula I is Form A-4 having an X-ray powder diffraction pattern shown in FIG. 4, with the peaks tabulated in Table 4.

In certain aspects, the solid form of Formula I is Form A-5 having an X-ray powder diffraction pattern shown in FIG. 5, with the peaks tabulated in Table 5.

In certain aspects, the solid form of Formula I is Form A-6 having an X-ray powder diffraction pattern shown in FIG. 6, with the peaks tabulated in Table 6.

In certain aspects, the solid form of Formula I is Form A-7 having an X-ray powder diffraction pattern shown in FIGS. 7, 8 and 9, with the peaks tabulated in Tables 7-9 respectively.

In certain aspects, the solid form of Formula I is Form A-8 having an X-ray powder diffraction pattern shown in FIG. 10, with the peaks tabulated in Table 10.

In certain aspects, the solid form of Formula I is Form A-9 having an X-ray powder diffraction pattern shown in FIG. 11, with the peaks tabulated in Table 11.

In certain aspects, the solid form of Formula I is Form A-10 having an X-ray powder diffraction pattern shown in FIG. 12, with the peaks tabulated in Table 12.

In certain aspects, the solid form of Formula I is Form A-11 having an X-ray powder diffraction pattern shown in FIG. 13, with the peaks tabulated in Table 13.

In certain aspects, the solid form of Formula I is Form A-12 having an X-ray powder diffraction pattern shown in FIG. 14, with the peaks tabulated in Table 14.

In certain aspects, the solid form of Formula I is Form A-13 having an X-ray powder diffraction pattern shown in FIG. 15, with the peaks tabulated in Table 15.

In certain aspects, the polymorphs described herein are substantially pure. A polymorph may comprise, consist essentially of, or consist of a compound of Formula I. In other aspects, the polymorphs may be mixtures of polymorphs, or co-crystals, or mixtures of crystalline and amorphous forms in various proportions.

In another embodiment, the present disclosure provides a method for kidney ureter imaging, the method comprising: administering to a subject a composition comprising a diagnostic effective amount of a polymorph of Formula I:

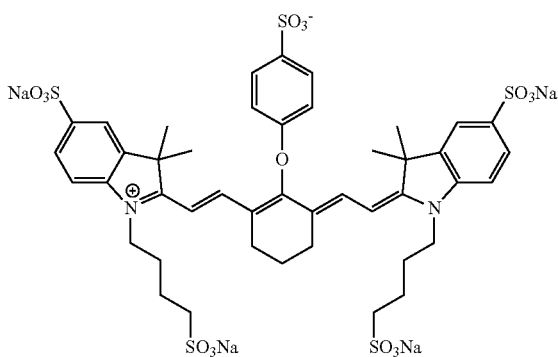

(I)

wherein the polymorph is selected from A-1 to A-13, wherein the administering is performed at one or more times selected from the group consisting of before a procedure, during a procedure, after a procedure and combinations thereof, exposing tissue of the subject's renal system to electromagnetic radiation (e.g., infrared light); and detecting fluorescence radiation from the compound.

In certain aspects, the administering is conducted intravenously.

In one embodiment, the present disclosure provides a pharmaceutical composition comprising a diagnostic imaging amount of a polymorph of Formula I; and a pharmaceutically acceptable carrier.

In certain aspects, the polymorph is any of the polymorphs described herein.

In yet another embodiment, the present disclosure provides a kit comprising a pharmaceutical composition, which comprises a polymorph described herein and an instruction manual.

In still yet another embodiment, the present disclosure provides a method for making a compound selected from Form A-1 to A-13 of Formula I:

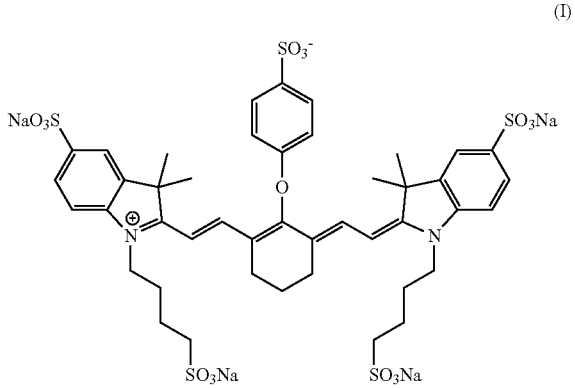

(I)

wherein the method comprises:
  dissolving a substantially pure form of Formula I in a solvent system to produce an admixture;
  optionally seeding the admixture;
  adding an anti-solvent to produce a slurry; and
  filtering the final slurry to produce the compound of Form A-1 to A-13 of Formula I.

Other embodiments, aspects, and objects will become better understood when read with the detailed description and drawings which follow.

DETAILED DESCRIPTION

I. Definitions

Figure 1A:
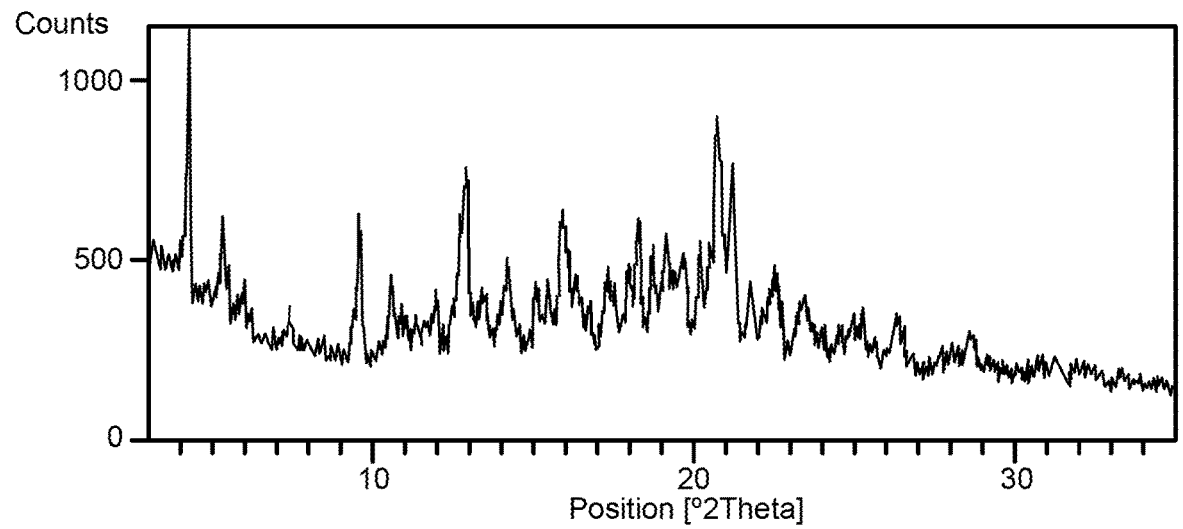
FIG. 1A shows an X-ray powder diffraction (XRPD) pattern of a solid form of Formula I which is form A-1, Pattern 1.

The terms "a," "an," or "the" as used herein not only include aspects with one member, but also include aspects with more than one member. For example, an embodiment of a method of imaging that comprises using a compound set forth herein would include an aspect in which the method comprises using two or more compounds set forth herein.

The term "approximately" or "about" as used herein to modify a numerical value indicates a defined range around that value. If "X" were the value, "approximately X" or "about X" would indicate a value from 0.9X to 1.1X, and more preferably, a value from 0.95X to 1.05X. Any reference to "approximately X" or "about X" specifically indicates at least the values X, 0.95X, 0.96X, 0.97X, 0.98X, 0.99X, 1.01X, 1.02X, 1.03X, 1.04X, and 1.05X. For example, "approximately X" or "about X" is intended to teach and provide written description support for a claim limitation of, e.g., "0.98X."

When the quantity "X" only allows whole-integer values (e.g., "X carbons") and X is at most 15, "about X" indicates from (X−1) to (X+1). In this case, "about X" as used herein specifically indicates at least the values X, X−1, and X+1. If X is at least 16, the values of 0.90X and 1.10X are rounded to the nearest whole-integer values to define the boundaries of the range.

When the modifier "approximately" or "about" is applied to describe the beginning of a numerical range, it applies to both ends of the range. Thus, "from approximately 700 to 850 nm" is equivalent to "from approximately 700 nm to approximately 850 nm." Thus, "from about 700 to 850 nm" is equivalent to "from about 700 nm to about 850 nm." When "approximately" or "about" is applied to describe the first value of a set of values, it applies to all values in that set. Thus, "about 680, 700, or 750 nm" is equivalent to "about 680 nm, about 700 nm, or about 750 nm."

"Balanced charge" as used herein includes the condition that the net charge for a compound and its associated counterions be zero under standard physiological conditions. In order to achieve a balanced charge, a skilled person will understand that after the first additional sulfonato group that balances the +1 charge of the indolinium ring, a cationic counterion (e.g., the cation of a Group I metal such as sodium) must be added to balance the negative charge from additional sulfonato groups. Similarly, anionic counterions must be added to balance any additional cationic groups (e.g., most basic amino groups under physiological conditions).

II. Embodiments

While preferred embodiments of the disclosure are shown and described herein, such embodiments are provided by way of example only and are not intended to otherwise limit the scope of the invention. Various alternatives to the described embodiments of the disclosure may be employed in practicing them.

Some advantages of cyanine dyes include: (1) cyanine dyes strongly absorb and fluoresce light; (2) many cyanine dyes do not rapidly photo-bleach under the fluorescence microscope; (3) many structures and synthetic procedures are available and the class of dyes is versatile; and (4) cyanine dyes are relatively small (a typical molecular weight is about 1,000 daltons) so they do not cause appreciable steric interference.

Generally, cyanine dyes are prepared according to the procedures taught in Hamer, F. M., *Cyanine Dyes and Related Compounds*, Weissberger, Mass., ed. Wiley Interscience, N.Y. 1964. For example, U.S. Pat. Nos. 6,663,847; 6,887,854; 6,995,274; 7,504,089; 7,547,721; 7,597,878 and 8,303,936, incorporated herein by reference, describe synthesis mechanisms for a variety of cyanine dyes.

Other cyanine dyes are known which contain reactive functional groups. For example, U.S. Pat. Nos. 4,337,063; 4,404,289 and 4,405,711, incorporated herein by reference, describe a synthesis for a variety of cyanine dyes having N-hydroxysuccinimide active ester groups. U.S. Pat. No. 4,981,977, incorporated herein by reference, describes a synthesis for cyanine dyes having carboxylic acid groups. U.S. Pat. No. 5,268,486, incorporated herein by reference, discloses a method for making arylsulfonate cyanine dyes. U.S. Pat. No. 6,027,709, incorporated herein by reference, discloses methods for making cyanine dyes having phosphoramidite groups. U.S. Pat. No. 6,048,982, incorporated herein by reference, discloses methods for making cyanine dyes having a reactive group selected from the group consisting of isothiocyanate, isocyanate, phosphoramidite, monochlorotriazine, dichlorotriazine, mono- or di-halogen substituted pyridine, mono- or di-halogen substituted diazine, aziridine, sulfonyl halide, acid halide, hydroxysuccinimide ester, hydroxy sulfosuccinimide ester, imido ester, glyoxal and aldehyde.

In one embodiment, the present disclosure provides a solid form, which solid form is Form A-1 of Formula I:

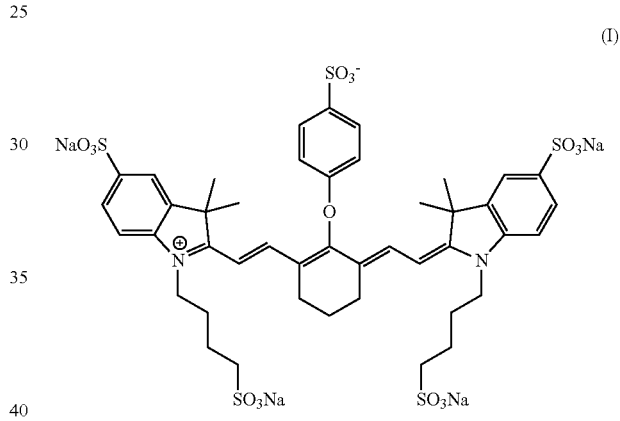

(I)

having an X-ray powder diffraction pattern shown in FIG. 1A, Pattern 1. In certain aspects, the disclosure provides a crystalline form of the compound of Formula I, characterized by an X-ray powder diffraction (XRPD) pattern comprising peaks at 4.2561, 9.6141, 12.8879, 18.7236 and 20.7367 degrees 2θ (+0.1 or +0.2 degrees 2θ), wherein said XRPD is made using CuK radiation. Other peaks appear in Table 1A.

Figure 1B:
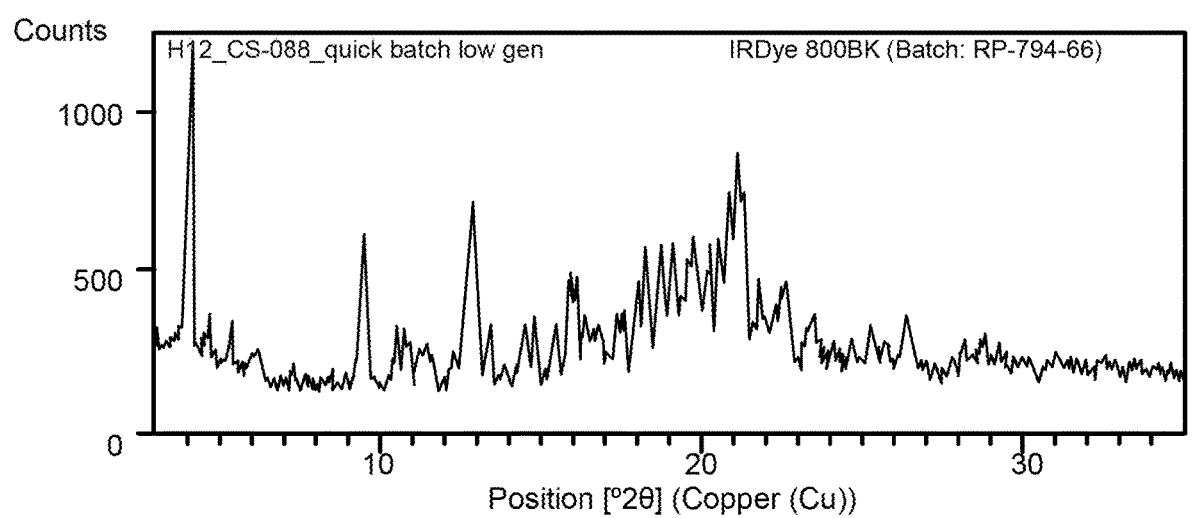
FIG. 1B shows an X-ray powder diffraction (XRPD) pattern of a solid form of Formula I which is form A-1, Pattern 1.

In certain aspects, the present disclosure provides a solid form, which solid form is Form A-1 of Formula I. Form A-1 of Formula I has an X-ray powder diffraction pattern shown in FIG. 1B, Pattern 1. In certain aspects, the disclosure provides a crystalline form of the compound of Formula I, characterized by an X-ray powder diffraction (XRPD) pattern comprising peaks at 4.29, 9.60, 12.93, 18.74 and 20.80 degrees 2θ (+0.1 or +0.2 degrees 2θ), wherein said XRPD is made using CuK radiation. Other peaks appear in Table 1B.

Figure 2:
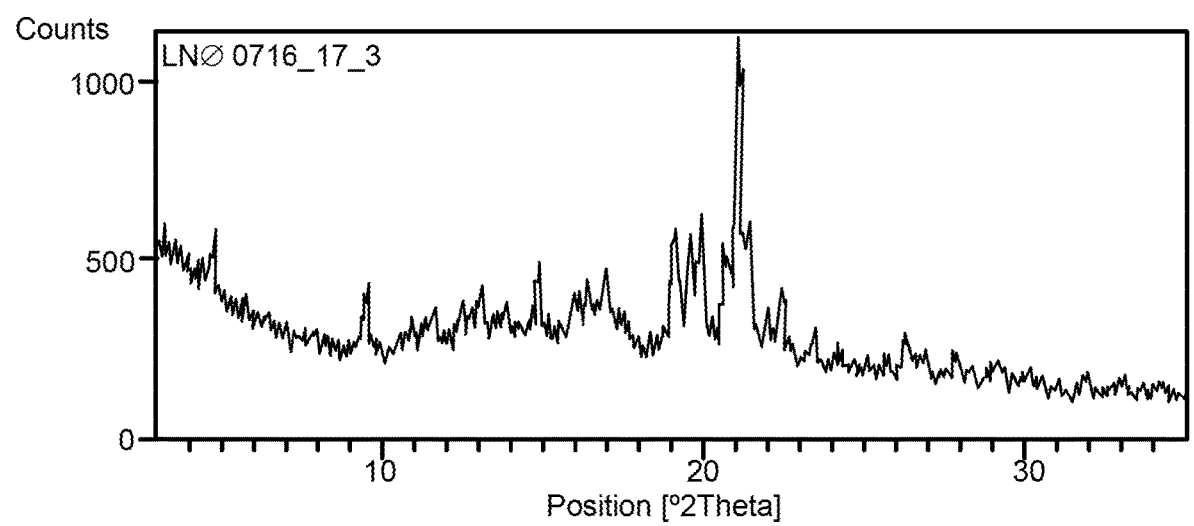
FIG. 2 shows an X-ray powder diffraction (XRPD) pattern of a solid form of Formula I which is form A-2, Pattern 2.

In certain aspects, the solid form of Formula I is Form A-2 having an X-ray powder diffraction pattern shown in FIG. 2, Pattern 2. In certain aspects, the disclosure provides a crystalline form of the compound of Formula I, characterized by an X-ray powder diffraction (XRPD) pattern comprising peaks at 21.0201, 21.3092, 21.9298 and 16.4226 degrees 2θ (±0.1 or +0.2 degrees 2θ), wherein said XRPD is made using CuK radiation. Other peaks appear in Table 2.

Figure 3:
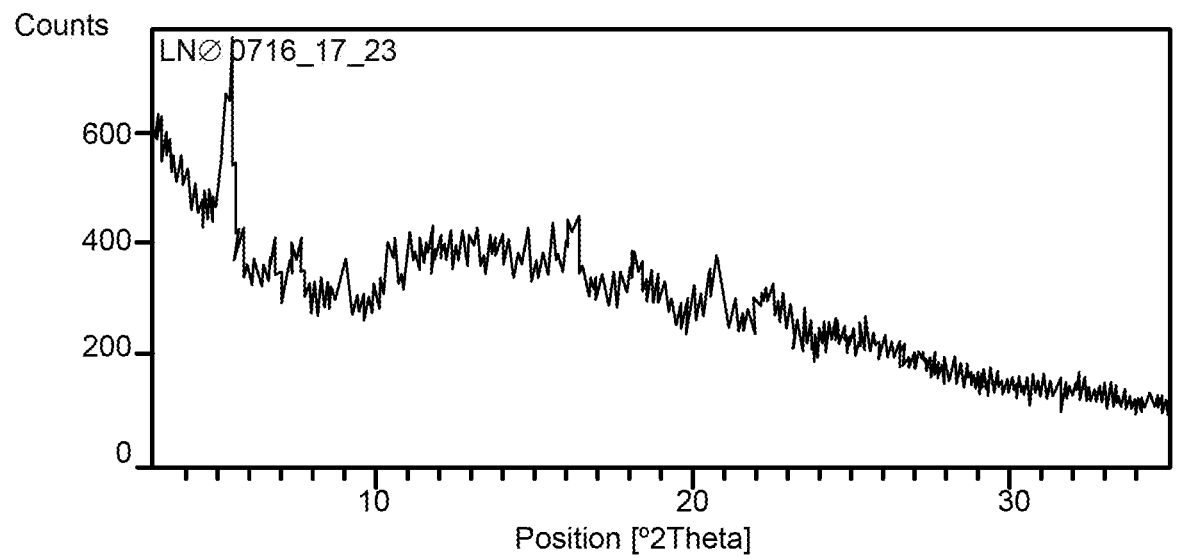
FIG. 3 shows an X-ray powder diffraction (XRPD) pattern of a solid form of Formula I which is form A-3, Pattern 3.

In certain aspects, the solid form of Formula I is Form A-3 having an X-ray powder diffraction pattern shown in FIG. 3, Pattern 3. In certain aspects, the disclosure provides a crystalline form of the compound of Formula I, characterized by an X-ray powder diffraction (XRPD) pattern comprising peaks at 5.4582, 8.9758, 15.5042, 18.0678 degrees 2θ (+0.1 or +0.2 degrees 2θ), wherein said XRPD is made using CuK radiation. Other peaks appear in Table 3.

Figure 4:
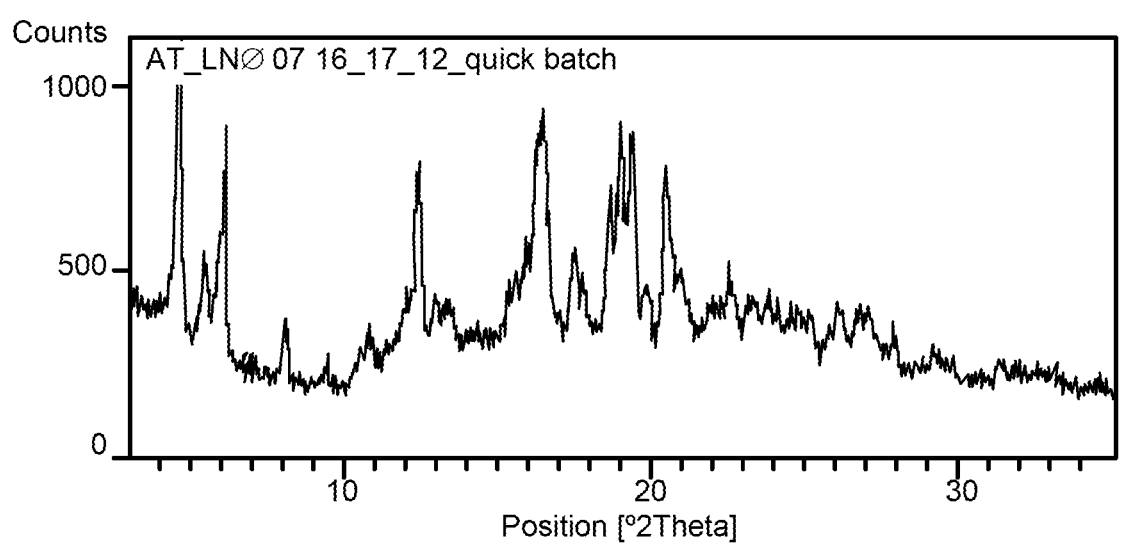
FIG. 4 shows an X-ray powder diffraction (XRPD) pattern of a solid form of Formula I which is form A-4, Pattern 4.

In certain aspects, the solid form of Formula I is Form A-4 having an X-ray powder diffraction pattern shown in FIG. 4, Pattern 4. In certain aspects, the disclosure provides a crystalline form of the compound of Formula I, characterized by an X-ray powder diffraction (XRPD) pattern comprising peaks at 4.6095, 6.1473, 11.9990, 12.4243, 16.4064, and 20.4115 degrees 2θ (±0.1 or +0.2 degrees 2θ), wherein said XRPD is made using CuK radiation. Other peaks appear in Table 4.

Figure 5:
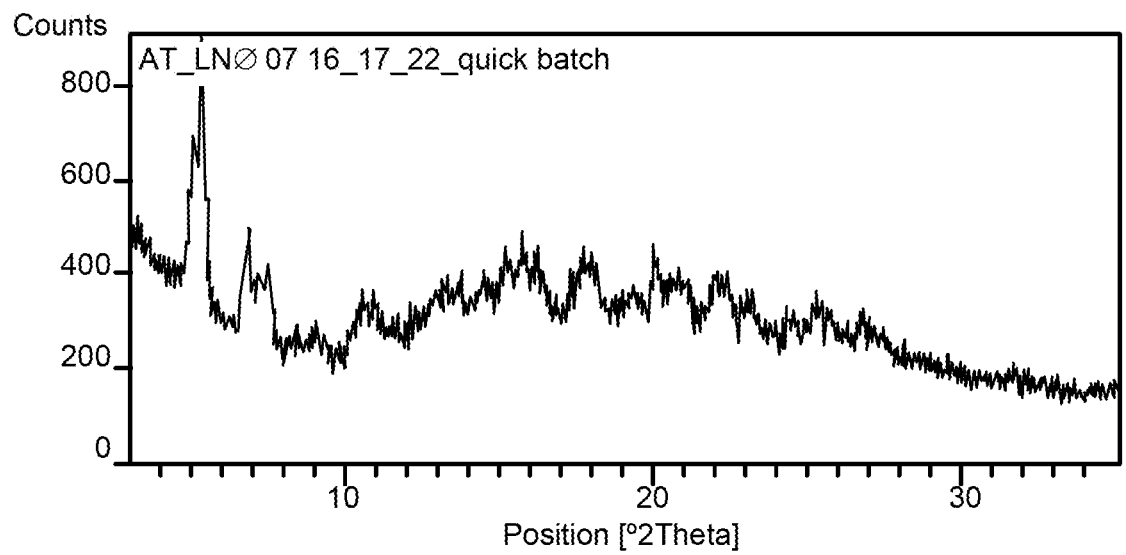
FIG. 5 shows an X-ray powder diffraction (XRPD) pattern of a solid form of Formula I which is form A-5, Pattern 5.

In certain aspects, the solid form of Formula I is Form A-5 having an X-ray powder diffraction pattern shown in FIG. 5, Pattern 5. In certain aspects, the disclosure provides a crystalline form of the compound of Formula I, characterized by an X-ray powder diffraction (XRPD) pattern comprising peaks at 5.0928, 5.3751, 7.1146, and 19.2858 degrees 2θ (+0.1 or +0.2 degrees 2θ), wherein said XRPD is made using CuK radiation. Other peaks appear in Table 5.

Figure 6:
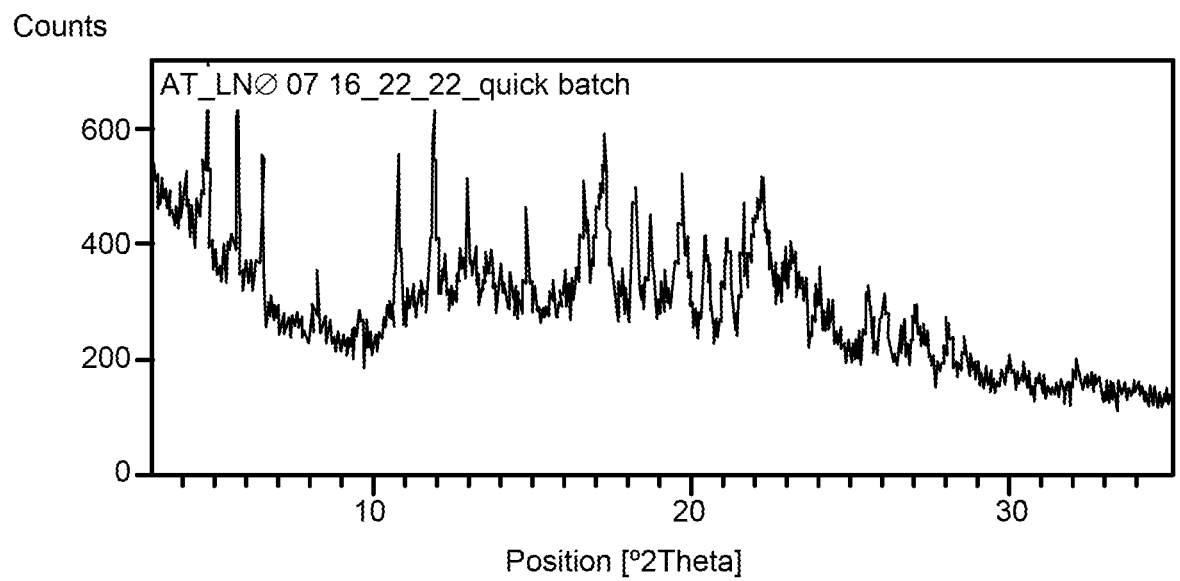
FIG. 6 shows an X-ray powder diffraction (XRPD) pattern of a solid form of Formula I which is form A-6, Pattern 6.

In certain aspects, the solid form of Formula I is Form A-6 having an X-ray powder diffraction pattern shown in FIG. 6, Pattern 6. In certain aspects, the disclosure provides a crystalline form of the compound of Formula I, characterized by an X-ray powder diffraction (XRPD) pattern comprising peaks at 11.8430, 4.7214, 5.6359, 10.7093, 11.8430, 17.1609 and 18.1502 degrees 2θ (+0.1 or +0.2 degrees 2θ), wherein said XRPD is made using CuK radiation. Other peaks appear in Table 6.

Figure 7:
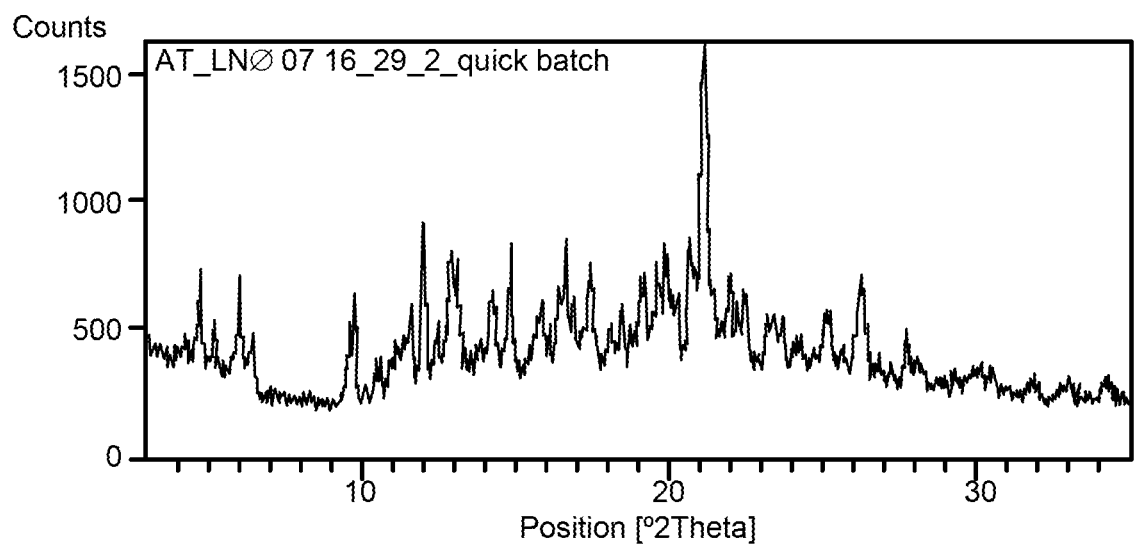
FIG. 7 shows an X-ray powder diffraction (XRPD) pattern of a solid form of Formula I which is form A-7, Pattern 7.

In certain aspects, the solid form of Formula I is Form A-7 having an X-ray powder diffraction pattern shown in FIG. 7, Pattern 7. In certain aspects, the disclosure provides a crystalline form of the compound of Formula I, characterized by an X-ray powder diffraction (XRPD) pattern comprising peaks at 21.1726, 21.0470, 11.9862, and 5.9858 degrees 2θ (±0.1 or ±0.2 degrees 2θ), wherein said XRPD is made using CuK radiation. Other peaks appear in Table 7.

Figure 8:
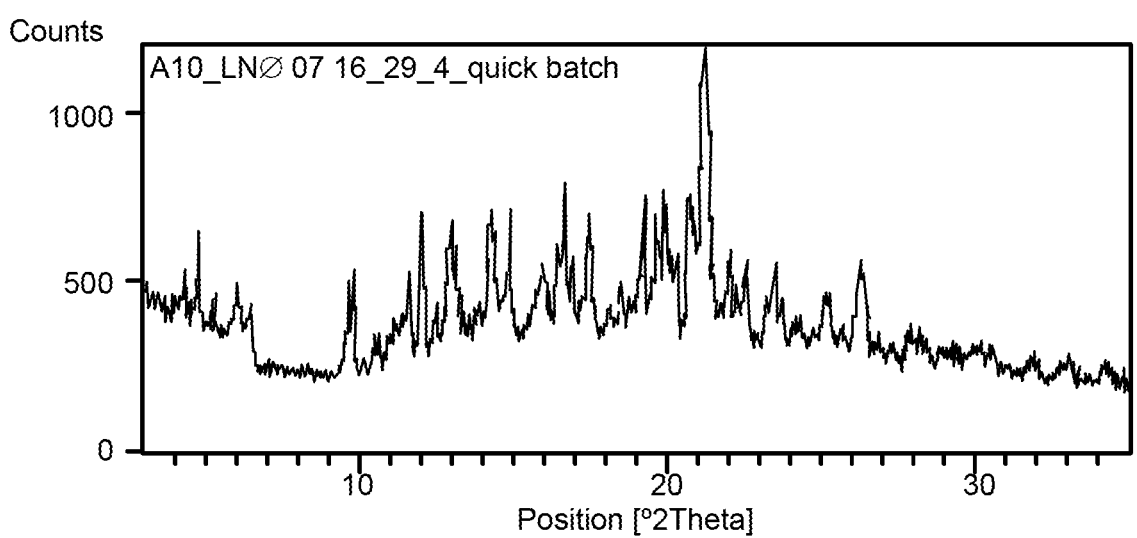
FIG. 8 shows an X-ray powder diffraction (XRPD) pattern of a solid form of Formula I which is form A-7, Pattern 7.

In certain aspects, the solid form of Formula I is Form A-7 having an X-ray powder diffraction pattern shown in FIG. 8, Pattern 7 example 2. In certain aspects, the disclosure provides a crystalline form of the compound of Formula I, characterized by an X-ray powder diffraction (XRPD) pattern comprising peaks at 21.0630, 19.8202, 19.1703, 19.0409, 12.8775, and 9.5680 degrees 2θ (±0.1 or ±0.2 degrees 2θ), wherein said XRPD is made using CuK radiation. Other peaks appear in Table 8.

Figure 9:
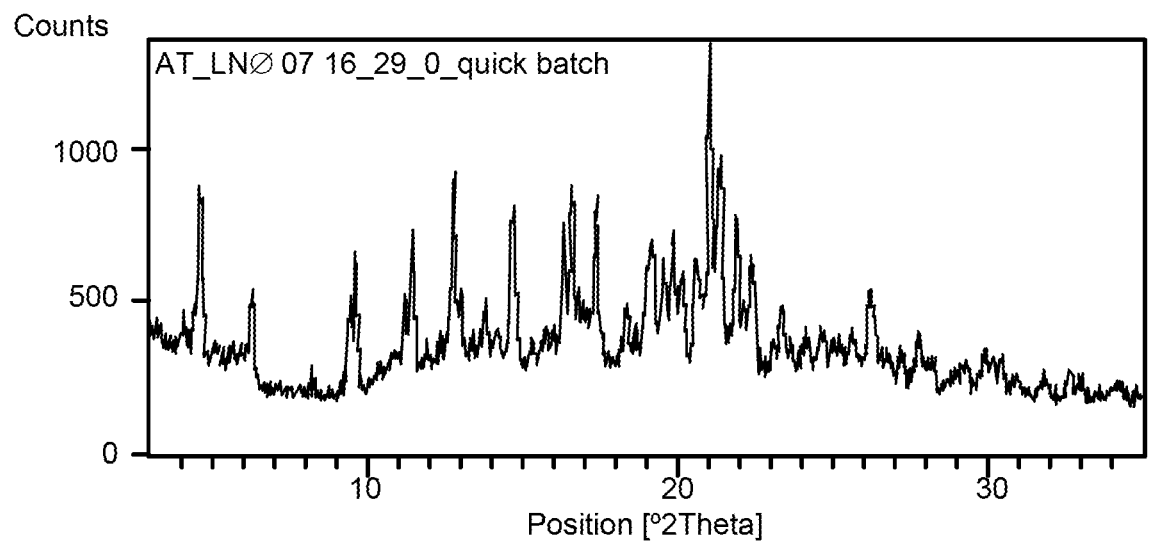
FIG. 9 shows an X-ray powder diffraction (XRPD) pattern of a solid form of Formula I which is form A-7, Pattern 7.

In certain aspects, the solid form of Formula I is Form A-7 having an X-ray powder diffraction pattern shown in FIG. 9, Pattern 7, Example 3. In certain aspects, the disclosure provides a crystalline form of the compound of Formula I, characterized by an X-ray powder diffraction (XRPD) pattern comprising peaks at 21.0557, 17.4402, and 12.8685 degrees 2θ (±0.1 or ±0.2 degrees 2θ), wherein said XRPD is made using CuK radiation. Other peaks appear in Table 9.

Figure 10:
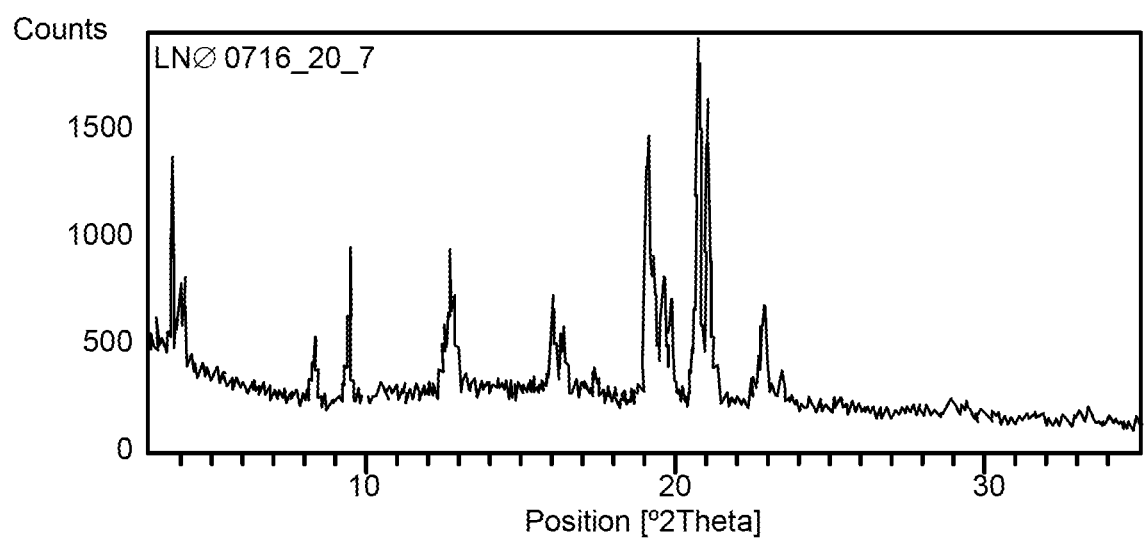
FIG. 10 shows an X-ray powder diffraction (XRPD) pattern of a solid form of Formula I which is form A-8, Pattern 8.

In certain aspects, the solid form of Formula I is Form A-8 having an X-ray powder diffraction pattern shown in FIG. 10, Pattern 8. In certain aspects, the disclosure provides a crystalline form of the compound of Formula I, characterized by an X-ray powder diffraction (XRPD) pattern comprising peaks 20.6831, 20.9865, and 19.0394 degrees 2θ (±0.1 or ±0.2 degrees 2θ), wherein said XRPD is made using CuK radiation. Other peaks appear in Table 10.

Figure 11:
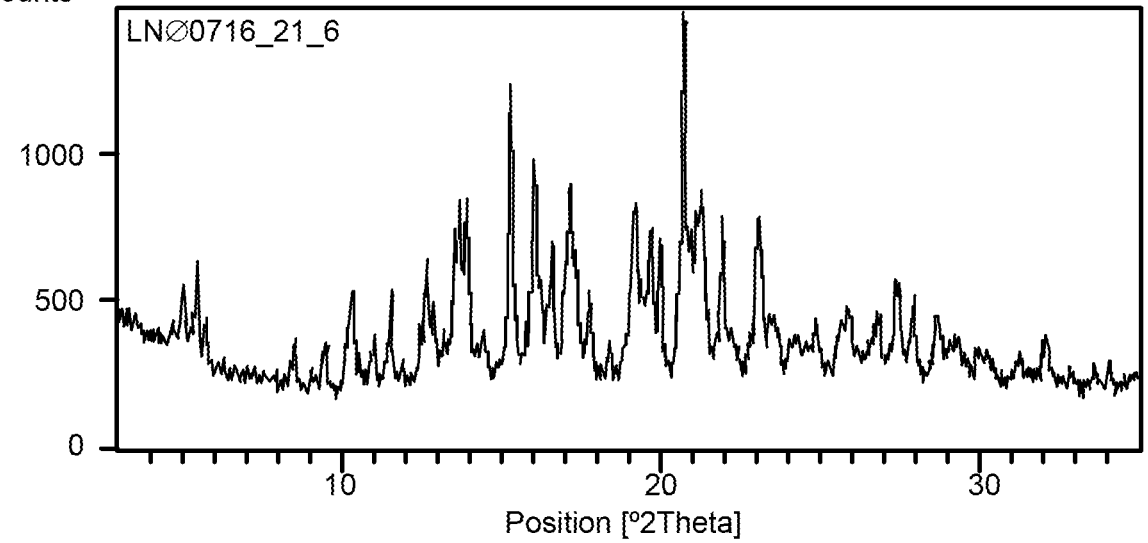
FIG. 11 shows an X-ray powder diffraction (XRPD) pattern of a solid form of Formula I which is form A-9, Pattern 9.

In certain aspects, the solid form of Formula I is Form A-9 having an X-ray powder diffraction pattern shown in FIG. 11, Pattern 9. In certain aspects, the disclosure provides a crystalline form of the compound of Formula I, characterized by an X-ray powder diffraction (XRPD) pattern comprising peaks 20.6988, 15.2962, 13.9016, and 13.7110 degrees 2θ (±0.1 or ±0.2 degrees 2θ), wherein said XRPD is made using CuK radiation. Other peaks appear in Table 11.

Figure 12:
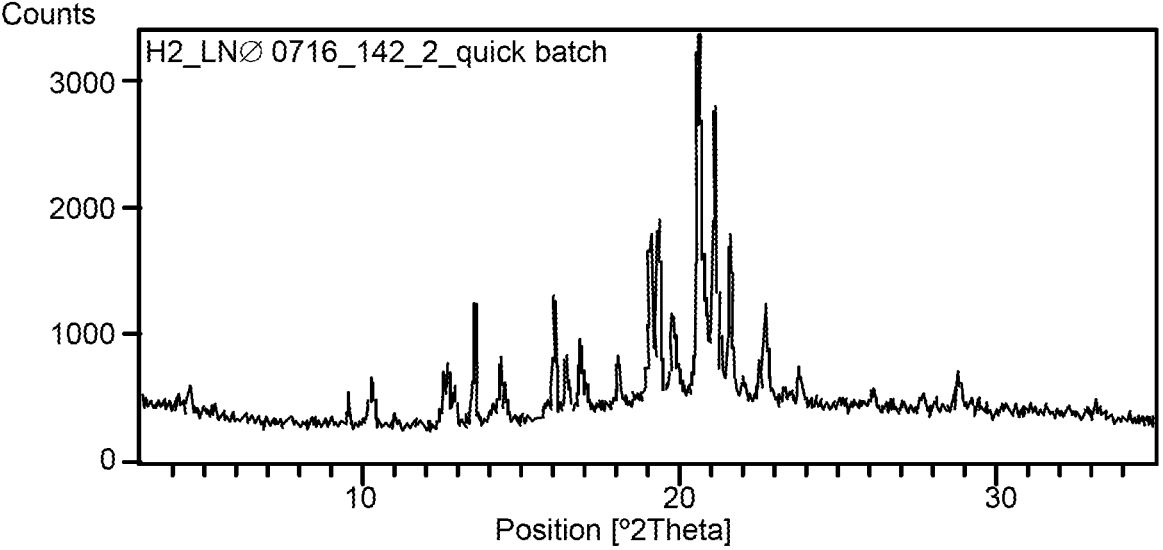
FIG. 12 shows an X-ray powder diffraction (XRPD) pattern of a solid form of Formula I which is form A-10, Pattern 10.

In certain aspects, the solid form of Formula I is Form A-10 having an X-ray powder diffraction pattern shown in FIG. 12, Pattern 10. In certain aspects, the disclosure provides a crystalline form of the compound of Formula I, characterized by an X-ray powder diffraction (XRPD) pattern comprising peaks 20.5520, 21.0470, 21.5370 and 19.0628 degrees 2θ (±0.1 or ±0.2 degrees 2θ), wherein said XRPD is made using CuK radiation. Other peaks appear in Table 12.

Figure 13:
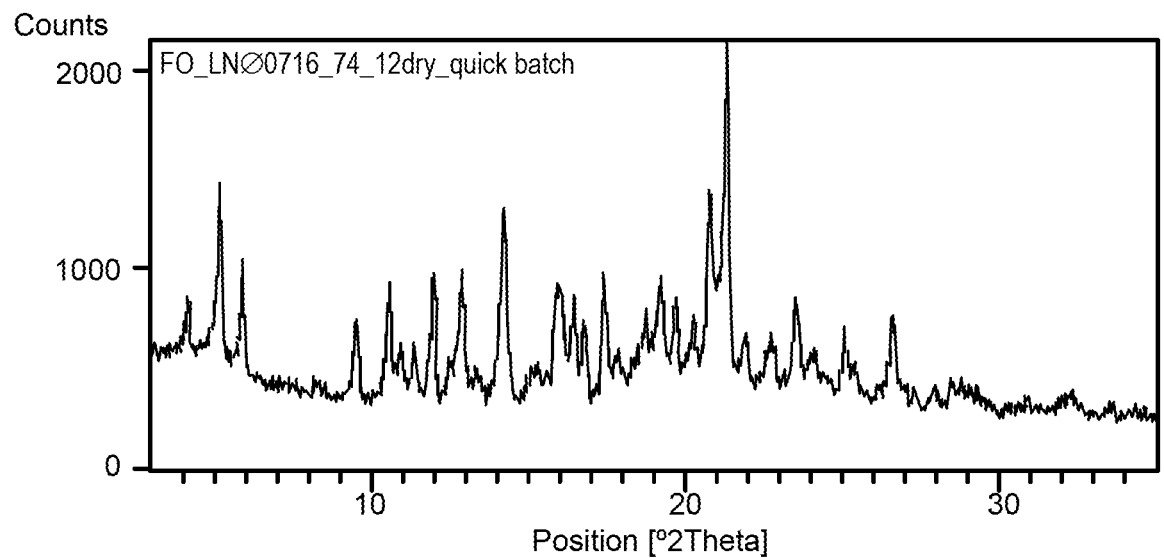
FIG. 13 shows an X-ray powder diffraction (XRPD) pattern of a solid form of Formula I which is form A-11, Pattern 11.

In certain aspects, the solid form of Formula I is Form A-11 having an X-ray powder diffraction pattern shown in FIG. 13, Pattern 11. In certain aspects, the disclosure provides a crystalline form of the compound of Formula I, characterized by an X-ray powder diffraction (XRPD) pattern comprising peaks 21.2861, 20.7567, 14.2428 and 5.3149 degrees 2θ (±0.1 or +0.2 degrees 2θ), wherein said XRPD is made using CuK radiation. Other peaks appear in Table 13.

Figure 14:
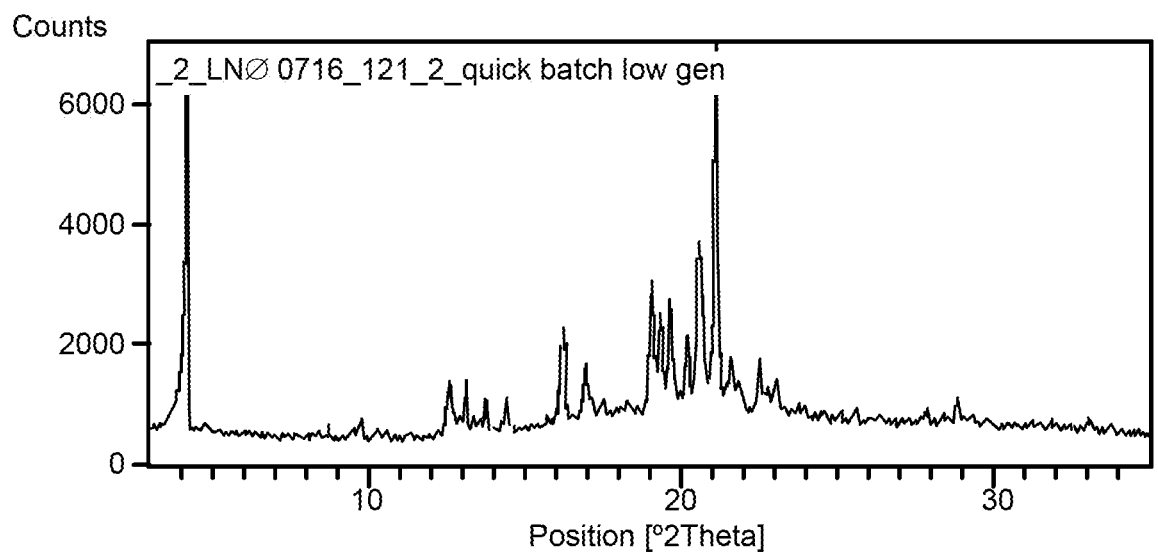
FIG. 14 shows an X-ray powder diffraction (XRPD) pattern of a solid form of Formula I which is form A-12, Pattern 12.

In certain aspects, the solid form of Formula I is Form A-12 having an X-ray powder diffraction pattern shown in FIG. 14, Pattern 12. In certain aspects, the disclosure provides a crystalline form of the compound of Formula I, characterized by an X-ray powder diffraction (XRPD) pattern comprising peaks 21.0467, 20.5000 and 4.1778 degrees 2θ (±0.1 or +0.2 degrees 2θ), wherein said XRPD is made using CuK radiation. Other peaks appear in Table 14.

Figure 15:
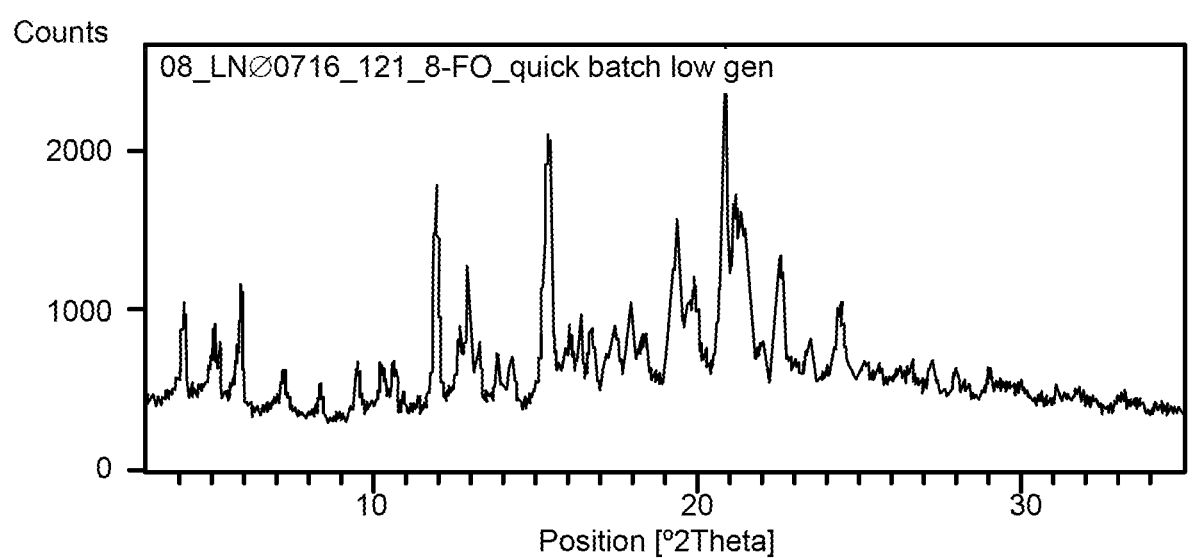
FIG. 15 shows an X-ray powder diffraction (XRPD) pattern of a solid form of Formula I which is form A-13, Pattern 13.

In certain aspects, the solid form of Formula I is Form A-13 having an X-ray powder diffraction pattern shown in FIG. 15, Pattern 13. In certain aspects, the disclosure provides a crystalline form of the compound of Formula I, characterized by an X-ray powder diffraction (XRPD) pattern comprising peaks 20.8110, 11.9583 and 19.3205 degrees 2θ (±0.1 or +0.2 degrees 2θ), wherein said XRPD is made using CuK radiation. Other peaks appear in Table 15.

In another embodiment, the present disclosure provides a method for kidney ureter imaging, the method comprising: administering to a subject a composition comprising a diagnostic effective amount of a polymorph of Formula I:

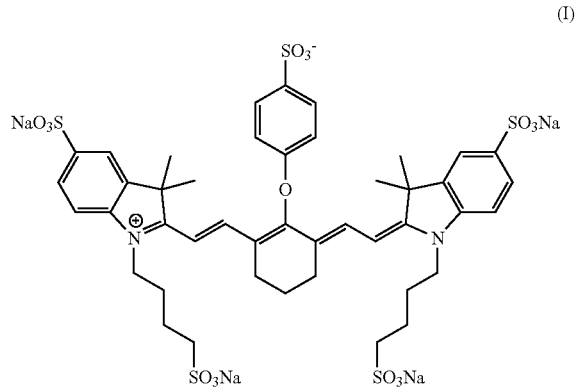

(I)

wherein the polymorph is selected from A-1 to A-13, wherein the administering is performed at one or more times selected from the group consisting of before a procedure, during a procedure, after a procedure and combinations thereof, exposing tissue of the subject's renal system to electromagnetic radiation; and detecting fluorescence radiation from the compound.

In certain aspects, the administering is conducted intravenously.

In another embodiment, the present disclosure provides a pharmaceutical composition comprising a diagnostic imaging amount of a polymorph of Formula I; and a pharmaceutically acceptable carrier.

In certain aspects, the polymorph is any of the polymorphs described herein.

In yet another embodiment, the present disclosure provides a kit comprising a pharmaceutical composition, which comprises a polymorph described herein and an instruction manual.

In certain aspects, the polymorphs of the disclosure are formulated into a composition such as a pharmaceutical composition prior to administration to a subject.

The compounds of Formula I can exist in crystalline or noncrystalline form, or as a mixture thereof. For salts of the disclosure that are in crystalline form, the skilled artisan will appreciate that pharmaceutically acceptable solvates or hydrates may be formed wherein solvent molecules are incorporated into the crystalline lattice during crystallization. Solvates may involve nonaqueous solvents such as ethanol, isopropanol, DMSO, acetic acid, ethanolamine, and ethylacetate. In one embodiment, the disclosure provides the sodium salt of the compound of Formula I incorporated into the crystalline lattice.

In one aspect, the present disclosure provides a polymorph of the compound of Formula I in isolated or pure form. "Isolated" or "pure" or "substantially pure" form refers to a sample in which the polymorph is present in an amount of >50%, >65%, >75%, or 80%, or 85% or more particularly >90%, >91%, >92%, >93%, >94%, >95%, >96%, >97%, >98%, or >99%, relative to other materials which may be present in the sample.

The polymorphs made according to the methods of the disclosure can be characterized by any methodology according to the art. For example, the polymorphs made according to the methods of the disclosure may be characterized by X-ray powder diffraction (XRPD), differential scanning calorimetry (DSC), thermogravimetric analysis (TGA), hot-stage microscopy, and spectroscopy (e.g., Raman, solid state nuclear magnetic resonance (ssNMR), and infrared (IR)).

X-Ray Powder Diffraction Patterns XRPD

Polymorphs according to the disclosure may be characterized by X-ray powder diffraction patterns (XRPD). The relative intensities of XRPD peaks can vary, depending upon the sample preparation technique, the sample mounting procedure and the particular instrument employed. Moreover, instrument variation and other factors can affect the 2θ values. Therefore, the XRPD peak assignments can vary by plus or minus about 0.2 degrees (±0.2 or +0.15 or +0.1).

The polymorph forms of the disclosure are useful in the production of imaging agents and can be obtained by means of a crystallization process to produce crystalline and semi-crystalline forms. In various embodiments, the crystallization is carried out by either generating the compound of Formula I in a reaction mixture and isolating the desired polymorph from the reaction mixture, or by dissolving raw compound in a solvent, optionally with heat, followed by crystallizing/solidifying the product by cooling (including active cooling) and/or by the addition of an antisolvent for a period of time. The crystallization can be followed by drying carried out under controlled conditions until the desired water or nonaqueous solvent content is reached in the end polymorphic form.

In another embodiment, the present disclosure provides a method of making a polymorph of a compound of Formula I (Form A-1, A-2, A-3, A-4, A-5, A-6, A-7, A-8, A-9, A-10, A-11, A-12, or A-13). In various embodiments, the disclosure is directed to methods of making a polymorph of the compound of Formula I, wherein the method involves converting an amorphous form into a desired polymorph. In certain embodiments, the methods comprise exposing a composition comprising an amorphous form to conditions sufficient to convert at least about 50% of the total amount of the amorphous form into at least about 50% of the desired polymorph, and isolating the desired polymorph as needed.

In certain instances, a crystalline solid will be more amenable to purification than an amorphous solid and the crystalline form is able to be made in higher purity. This is because, under proper conditions, the formation of the crystals tends to exclude impurities from the solid, in contrast to amorphous solids formed in a less controlled manner. Similarly, a crystalline solid will often have better stability than an amorphous solid, as the crystal packing gives a protective effect. For materials which are polymorphic, some crystal forms will normally be more effective than others at excluding impurities and enhancing stability.

In one embodiment, the method includes administering the compound of Formula I intravenously. The compound of Formula I can be administered as a bolus injection, e.g., an intravenous bolus injection. In some embodiments, about 0.1 mL to 5 mL such as 0.5, 0.9, 1, 2, 3, 4, or 5 mL or about 10 mL, or about 5, 6, 7, 8, 9 or about 10 mL of a composition comprising the compound of Formula I is administered in a bolus injection.

In one embodiment, the method includes administering the compound of Formula I wherein the pharmaceutically acceptable cation is selected from the group consisting of potassium or sodium.

In one embodiment, the method includes administering the compound of Formula I in combination with a pharmaceutically acceptable carrier selected from the group consisting of physiological sterile saline solution, sterile water solution, pyrogen-free water solution, isotonic saline solution or 0.5N or about 1.0N, and phosphate buffer solution. In certain instances, the formulation includes reconstitution of a lyophilized cake (about 25 mg 800 BK, mannitol and citric acid) into 10 mL of half-normal saline (0.45% aqueous NaCl).

The compound of Formula I can be highly soluble in water. In some embodiments, the compound of Formula I is re-suspended in water to a concentration of at least 200 mg/mL, or about 300 mg/mL to about 320 mg/mL.

In one embodiment, the method includes administering the compound of Formula I at a diagnostic effective amount of the compound ranging between approximately 3000.0 µg/kg and approximately 1500.0 µg/kg.

In one embodiment, the method includes administering the compound of Formula I at a diagnostic effective amount of the compound ranging between approximately 1500.0 µg/kg and approximately 1000.0 µg/kg.

In one embodiment, the method includes administering the compound of Formula I at a diagnostic effective amount of the compound ranging between approximately 1000.0 µg/kg and approximately 500.0 µg/kg.

In one embodiment, the method includes administering the compound of Formula I at a diagnostic effective amount of the compound ranging between approximately 500.0 µg/kg and approximately 170.0 µg/kg.

In one embodiment, the method includes administering the compound of Formula I at a diagnostic effective amount of the compound ranging between approximately 170.0 µg/kg and approximately 120.0 µg/kg.

In one embodiment, the method includes administering the compound of Formula I at a diagnostic effective amount of the compound ranging between approximately 120.0 µg/kg and approximately 60.0 µg/kg.

In one embodiment, the method includes administering the compound of Formula I at a diagnostic effective amount of the compound ranging between approximately 60.0 µg/kg and approximately 30.0 µg/kg.

In one embodiment, the method includes administering the compound of Formula I at a diagnostic effective amount of the compound ranging between approximately 30.0 µg/kg and approximately 1.0 µg/kg.

In one embodiment, the method includes administering the compound of Formula I at a diagnostic effective amount of the compound ranging between approximately 1.0 µg/kg and approximately 0.1 µg/kg.

In one embodiment, the method includes administering the compound of Formula I at a diagnostic effective amount of the compound ranging between approximately 0.1 µg/kg and approximately 0.01 µg/kg.

The compounds of Formula I can be non-toxic. They can absorb and fluoresce light, and do not rapidly photo-bleach under fluorescence imaging. Upon administration, the compounds of Formula I can be transported to tissues and organs of the subject via the natural flow of bodily fluids in the subject. As such, compounds of Formula I can be carried or transferred from the site of administration to the desired sites, tissues and organs for, e.g., visualization.

In certain embodiments, the compounds and methods herein can image the biliary tract which includes any part of the liver, gall bladder, spleen, small intestine, and associated ducts. In certain instances, the biliary tract includes the intrahepatic bile ducts, cystic duct-gallbladder to common bile duct—and common bile duct—liver and gallbladder to small intestine. In some instances, the compounds herein are found in a subject's bile or urine at a time period after administering. The present disclosure provides compositions of the compounds of Formula I in urine or bile.

In one embodiment, the organ includes one or more of kidney, bladder, liver, spleen, intestine, heart, lungs and muscle. In one embodiment, the organ is kidney, bladder or combinations thereof or surrounding structures. In another embodiment, the organ is the ureter of a kidney. The ureter is a tube that carries urine from the kidney to the urinary bladder. A human has two ureters, one attached to each kidney. The upper half of the ureter is located in the abdomen and the lower half is located in the pelvic area. In another aspect, the organ of interest is the urethra. The urethra is the tube from the bladder to the outside of the body.

In one embodiment, the diagnostic effective amount of the compound of Formula I is in the range from approximately 300.0 µg/kg to approximately 150.0 µg/kg.

In one embodiment, the diagnostic effective amount of the compound of Formula I is in the range from approximately 150.0 µg/kg to approximately 100.0 µg/kg.

In one embodiment, the diagnostic effective amount of the compound of Formula I is in the range from approximately 100.0 µg/kg to approximately 50.0 µg/kg.

In one embodiment, the diagnostic effective amount of the compound of Formula I is in the range from approximately 50.0 µg/kg to approximately 17.0 µg/kg.

In one embodiment, the diagnostic effective amount of the compound of Formula I is in the range from approximately 17.0 µg/kg to approximately 12.0 µg/kg.

In one embodiment, the diagnostic effective amount of the compound of Formula I is in the range from approximately 12.0 µg/kg to approximately 6.0 µg/kg.

In one embodiment, the diagnostic effective amount of the compound of Formula I is in the range from approximately 6.0 µg/kg to approximately 0.5 µg/kg.

The diagnostic effective amount of the compound of Formula I according to the disclosure is effective over a wide dosage range. The exact dosage will depend upon the route of administration, the form in which each compound is administered, the gender, age, and body weight of the subject to be treated, and the preference and experience of the administrator.

In selected embodiments, the fluorescence intensity of each of the administered compound of Formula I may be independently measured at a time period of, for example, less than 24 hrs, 23 hrs, 22 hrs, 21 hrs, 20 hrs, 19 hrs, 18 hrs, 17 hrs, 16 hrs, 15 hrs, 14 hrs, 13 hrs, 12 hrs, 11 hrs, 10 hrs, 9.5 hrs, 9.0 hrs, 8.5 hrs, 8.0 hrs, 7.5 hrs, 7.0 hrs, 6.5 hrs, 6.0 hrs, 5.5 hrs, 5.0 hrs, 4.75 hrs, 4.50 hrs, 4.25 hrs, 4.00 hrs, 3.75 hrs, 3.50 hrs, 3.25 hrs, 3.00 hrs, 2.75 hrs, 2.50 hrs, 2.25 hrs, 2.00 hrs, 1.75 hrs, 1.50 hrs, 1.25 hrs, 1.00 hrs, 0.90 hrs, 0.80 hrs, 0.70 hrs, 0.60 hrs, 0.50 hrs, 0.40 hrs, 0.30 hrs, 0.20 hrs, or immediately after administering.

In selected embodiments, the fluorescence intensity of each of the administered compound of Formula I may be independently measured at a time period of, for example, greater than 23 hrs, 22 hrs, 21 hrs, 20 hrs, 19 hrs, 18 hrs, 17 hrs, 16 hrs, 15 hrs, 14 hrs, 13 hrs, 12 hrs, 11 hrs, 10 hrs, 9.5 hrs, 9.0 hrs, 8.5 hrs, 8.0 hrs, 7.5 hrs, 7.0 hrs, 6.5 hrs, 6.0 hrs, 5.5 hrs, 5.0 hrs, 4.75 hrs, 4.50 hrs, 4.25 hrs, 4.00 hrs, 3.75 hrs, 3.50 hrs, 3.25 hrs, 3.00 hrs, 2.75 hrs, 2.50 hrs, 2.25 hrs, 2.00 hrs, 1.75 hrs, 1.50 hrs, 1.25 hrs, 1.00 hrs, 0.90 hrs, 0.80 hrs, 0.70 hrs, 0.60 hrs, 0.50 hrs, 0.40 hrs, 0.30 hrs, 0.20 hrs, 0.10 hrs after administering.

In selected embodiments, the fluorescence intensity of each of the administered compound of Formula I may be independently measured at a time period in the range from approximately 0.10 hrs to approximately 24 hrs, approximately 0.20 hrs to approximately 23 hrs, approximately 0.30 hrs to approximately 22 hrs, approximately 0.40 hrs to approximately 21 hrs, approximately 0.50 hrs to approximately 20 hrs, approximately 0.60 hrs to approximately 19 hrs, approximately 0.70 hrs to approximately 18 hrs, approximately 0.80 hrs to approximately 17 hrs, approximately 0.90 hrs to approximately 16 hrs, approximately 1.00 hr to approximately 15 hrs, approximately 1.25 hrs to approximately 14 hrs, approximately 1.50 hrs to approximately 13 hrs, approximately 1.75 hrs to approximately 12 hrs, approximately 2.00 hrs to approximately 11 hrs, approximately 2.25 hrs to approximately 10 hrs, approximately 2.50 hrs to approximately 9.5 hrs, approximately 2.75 hrs to approximately 9.0 hrs, approximately 3.00 hrs to approximately 8.5 hrs, approximately 3.25 hrs to approximately 8.0 hrs, approximately 3.50 hrs to approximately 7.5 hrs, approximately 3.75 hrs to approximately 7.0 hrs, approximately 4.00 hrs to approximately 6.5 hrs, approximately 4.25 hrs to approximately 6.0 hrs, approximately 4.50 hrs to approximately 5.5 hrs, approximately 4.75 hrs to approximately 5.0 hrs after administering.

In the embodiments of the methods described herein, the sample is illuminated with a wavelength of light selected to give a detectable optical response, and observed with a means for detecting the optical response. Equipment that is useful for illuminating the dye compounds of the disclosure includes, but is not limited to, tungsten lamps, hand-held ultraviolet lamps, mercury arc lamps, xenon lamps, light emitting diodes (LED), lasers and laser diodes. These illumination sources are optionally integrated into surgical cameras, laparoscopes and microscopes. Preferred embodiments of the disclosure are dyes that are excitable at or near the wavelengths 633-636 nm, 647 nm, 660 nm, 680 nm and beyond 700 nm, such as 780 nm, 810 nm and 850 nm as these regions closely match the output of relatively inexpensive excitation sources. The optical response is optionally detected by visual inspection, or by use of any of the following devices: CCD cameras, video cameras, photographic film.

The NIR imaging probe used was the compound of Formula I; excitation 773 nm and emission 790 nm.

The compound of Formula I as described herein can be administered in a manner compatible with the dosage formulation, and in such amount as will be effective or suitable for in vivo imaging. The quantity to be administered depends on a variety of factors including, e.g., the age, body weight, physical activity, and diet of the individual, the tissue or organ to be imaged, and type of procedure or surgery to be performed. In certain embodiments, the size of the dose may also be determined by the existence, nature, and extent of any adverse side effects that accompany the administration of the compound in a particular individual.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

In certain embodiments, the dose may take the form of solid, semi-solid, or lyophilized powder forms, preferably in unit dosage forms suitable for simple administration of precise dosages. In some embodiments, the dose is provided in a container, vial or syringe at a particular dosage for one or more administrations.

As used herein, the term "unit dosage form" refers to physically discrete units suitable as unitary dosages for humans and other mammals, each unit containing a predetermined quantity of an imaging agent calculated to produce the desired onset, tolerability, and/or fluorescent effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the imaging agent.

Methods for preparing such dosage forms are known to those skilled in the art (see. e.g., *REMINGTON'S PHARMACEUTICAL SCIENCES*, 18th ED., Mack Publishing Co., Easton, Pa. (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., *REMINGTON'S PHARMACEUTICAL SCIENCES*, 18th ED., Mack Publishing Co., Easton, Pa. (1990)).

In certain embodiments, the dosage forms contain a stabilizing agent for the storage, isolation, purification, and/or lyophilization of the compounds. Agents for lyophilization include, but are not limited to, a saccharide such as a monosaccharide, a disaccharide or dextran. Other saccharides include glucose, galactose, xylose, glucuronic acid, trehalose, dextran, hydroxyethyl starch, mannitol, or 5% dextrose.

For parenteral administration, e.g., intravenous injection, intra-arterial injection, subcutaneous injection, intramuscular injection and the like, the effective dose can be in the form of sterile injectable solutions and sterile packaged powders. Preferably, injectable solutions are formulated at a pH of from about 4.5 to about 10 such as 4.6, 5, 6, 7, 8, 9 or 10, or physiological pH.

In some aspects, the effective dose of Formula I for imaging is directly administered into an organ or anatomical structure of interest. Suitable organs or anatomical structures include, for example, the kidney, bladder or combinations thereof or surrounding structures. In another embodiment, the organ is the ureter or urethra or a surrounding anatomical structure.

In some embodiments, the effective dose for imaging contains a lyophilized compound described herein in a high-quality, easily dissolved form which is stable for months at room temperature. The lyophilized compound of Formula I can be stored in any suitable type of sealed container, such as a sealed vial or syringe that contains an amount of the compound for a single dosage for a subject, such as a human adult. The term "vial" is used broadly herein, to refer to any drug-packaging device that is designed and suitable for sealed and sterile storage, shipping, and handling of small (e.g., single-dosage) quantities of drugs. Single-chamber vials (which would contain only the lyophilized compound, with no water) are well known; a typical single-chamber vial may be designed for use with an intravenous infusion bag. Alternatively, two-chamber vials can be used that contain both the lyophilized compound and a sterile aqueous solution, to enable immediate reconstitution and injection of an aqueous liquid containing the compound of Formula I.

In certain instances, the reconstituted solution, which is injectable, contains an acid, such as an organic acid or inorganic acid. Suitable acids include, but are not limited to, phosphoric acid, citric acid, malic acid, tartaric acid, lactic acid, formic acid, ascorbic acid, fumaric acid, gluconic acid, succinic acid, maleic acid, adipic acid, and any mixture thereof. Other suitable acids include, but are not limited to, hydrochloric acid, bromic acid, nitric acid, sulfuric acid, perchloric acid, acetic acid, lactic acid, glycolic acid, succinic acid, tartaric acid, galacturonic acid, embonic acid, glutamic acid, aspartic acid, oxalic acid, D- or L-malic acid, methanesulfonic acid, ethanesulfonic acid, 4-toluenesulfonic acid, salicylic acid, benzoic acid, malonic acid, and mixtures thereof.

The amount of acid is typically 0.50 mg/mL to about 12.0 mg/mL (w/v). For example, the amount of acid can be about 1.50 to about 10.0 mg/mL or about 1.90 to about 9.8 or about 1.92 mg to about 9.6 mg or about 1.92 mg/mL (w/v).

In one aspect, the acid is anhydrous citric acid at about 1.92 mg/mL to about 9.6 mg/mL.

In certain instances, the lyophilized powder is then reconstituted for injection with water, buffer or saline. In certain instances, the pH of the solution is between about 6.0 to about 8.5, such as 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, or 8.5. In certain instances, the pH of the reconstituted solution is about 7.0 to 7.8, or about 7.1 to 7.6 or about 7.3 to about 7.5 such as 7.4.

The saline can be 0.1N to about 2.0N or about 0.5N to about 1.5N or about 1N saline.

In certain instances, the reconstituted solution contains a sugar or sugar alcohol, which can be D or L or DL configuration. Suitable sugars include, but are not limited to, erythritol, tagatose, sucrose, fructose, glucose, sorbitol, mannitol, maltitol, xylitol, glycyrrhizin, malitol, maltose, lactose, xylose, arabinose, isomalt, lactitol, trehalulose, ribose, and any mixture thereof.

The amount of sugar is typically about 10 mg/mL to about 500 mg/mL or about 20 mg/mL to about 400 mg/mL or about 40 mg/mL to about 250 mg/mL or about 42.8 mg/mL to about 214 mg/mL or about 42.8 mg/mL.

In one aspect, the sugar is D-mannitol which is used at about 42.8 mg/mL to about 214 mg/mL such as 42.8 mg/mL.

In certain aspects, the Dye of Formula I is present at about 0.5 mg/mL to about 20 mg/mL, such as 1, 2, 3, 4, 5, 6, 7, 8, 9, 10, 11, 12, 13, 14, 15, 16, 17, 18, 19, or about 20 mg/mL. In certain instances the amount of compound of Formula I is about 0.5 to about 10 mg/mL or about 1 mg/mL to about 7 mg/mL or about 1 mg/mL to about 5 mg/mL. The vial may be about 1-10 mL or about 1 to about 5 mL which is about 5 mg/vial-25 mg/vial at 5 mg/mL.

In one embodiment, the method includes administering the compound of Formula I in combination with a pharmaceutically acceptable carrier selected from the group consisting of physiological sterile saline solution, sterile water solution, pyrogen-free water solution, isotonic saline solution or 0.5N or about 1.0N, and phosphate buffer solution. In certain instances, the formulation includes reconstitution of a lyophilized cake (about 25 mg 800 BK, mannitol and citric acid) into 10 mL of half-normal saline (0.45% aqueous NaCl).

In one embodiment, the method includes administering the compound of Formula I in combination with a pharmaceutically acceptable carrier selected from the group consisting of physiological sterile saline solution, sterile water solution, pyrogen-free water solution, isotonic saline solution or 0.5N or about 1.0N, and phosphate buffer solution. In certain instances, the formulation includes reconstitution of a lyophilized cake having D-mannitol-42.8 mg-214 mg (e.g., 42.8 mg/mL); Citric Acid, Anhydrous-1.92 mg-9.6 mg (e.g., 1.92 mg/mL) at a pH 7.4 (Range 7.3-7.5).

Provided herein are kits containing a compound of Formula I. In some embodiments, a kit comprises one or more vials or syringes containing compound of Formula I in, for example, a lyophilized form. Such kits can also include a pharmaceutically acceptable carrier or a sterile aqueous solution, e.g., sterile water for reconstituting the compound prior to administration. In some cases, the kit also includes a sterile syringe for parenteral administration of the compound or for use with an intravenous infusion bag. The kit can also include an instruction manual for use.

In certain embodiments, the present disclosure provides a method for making a compound selected from Form A-1 to A-13 of Formula I:

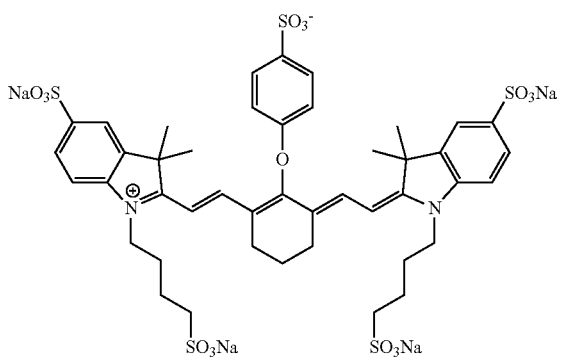

wherein the method comprises:
dissolving a substantially pure form of Formula I in a solvent system to produce an admixture;
optionally seeding the admixture;
adding an anti-solvent to produce a slurry; and
filtering the final slurry to produce the compound of Form A-1 to A-13 of Formula I.

In certain aspects, a substantially pure form of a compound of Formula I can be crystalline, amorphous, non-crystalline, solid, mixture of forms, or any combination of the forgoing. Any one of these forms can be dissolved in the organic solvent system.

In certain aspects, the solvent system comprises an organic solvent and water. In certain aspects, the organic solvent is present from about 5% v/v to about 95% v/v. In certain aspects, the organic solvent is present from about 5% v/v to about 50% v/v, or from about 50% v/v to about 80% v/v. In other aspects, the organic solvent is present from about 35% v/v to about 70% v/v, or 40% v/v to about 60% v/v, or from about 45% v/v to about 55% v/v.

In certain aspects, the solvent system comprises water from about 5% v/v to about 95% v/v, or from about 5% v/v to about 50% v/v, or from about 50% v/v to about 80% v/v.

In certain aspects, the organic solvent is acetone or a $C_1$-$C_6$ alkanol. The $C_1$-$C_6$ alkanol is selected from methanol, ethanol, propanol, butanol, pentanol, hexanol and mixtures thereof. All the isomers of the alkanols are also included such as 1-propanol, 2-propanol, 1-butanol, 2-butanol, 3-butanol, 1-pentanol, 2-pentanol and the like.

In certain aspects, the anti-solvent is an organic solvent such as acetone or a $C_1$-$C_6$ alkanol.

In certain aspects, dissolving the non-crystalline form of Formula I comprises heating the sample from about 25° C. to about 70° C., or from about 35° C. to about 70° C., or from about 40° C. to about 60° C., or from about 45° C. to about 55° C.

In certain aspects, a seed crystal may optionally be added to the solution to promote crystallization. Any of the forms can be added as a seed crystal such as Form A1 to Form A13, such as A1, A2, A3, A4, A5, A6, A7, A8, A9, A10, A11, A12, or Form A13.

In principle, addition of the seed crystal may be during stirring or the seed crystals are added after stirring. In certain aspects, a seed crystal may optionally be added before the solution is cooled. Seed crystals can be used to promote conversion and/or increase the rate of conversion of one polymorph into another. The polymorph conversion reactions are often made through agitation by a variety of methods. The form of agitation can be from shaking the reaction vessel or by stirring with a magnetic or mechanical stirrer. The polymorph conversion reactions can also be effectuated by the boiling action of the solvent.

In certain aspects, after the form of Formula I is dissolved, the admixture is cooled. A crystallization temperature is not limited, but preferable results can be obtained by carrying out crystallization usually at a temperature of ice-cold water bath, room temperature or a temperature of warm water bath. Addition of seed crystals is also arbitrary, but with the addition of them, the desired polymorphic crystals can be obtained reliably in a shorter time.

In certain aspects, the compound produced is a member selected form the group consisting of Form A1 to Form A13, such as A1, A2, A3, A4, A5, A6, A7, A8, A9, A10, A11, A12, or Form A13.

When ranges are used herein, all combinations and sub-combinations of ranges and specific embodiments therein are intended to be included. Use of the term "approximately" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments that "consist of" or "consist essentially of" the described features.

EXAMPLES

The following examples are offered to illustrate, but not to limit the claimed disclosure.

Example 1: Synthesis/Crystalline Samples for Analysis

The compound of Formula I may be synthesized by dissolving 3,3-Dimethyl-2-[2-[2-chloro-3-[2-[1,3-dihydro-3,3-dimethyl-5-sulfo-1-(4-sulfobutyl)-2H-indol-2-ylidene]-ethylidene]-1-cyclohexen-1-yl]-ethenyl]-5-sulfo-1-(4-sulfobutyl)-3H-indolium hydroxide, innersalt, trisodium salt (1 g, 1.05 mmol) in 25 mL of water and sparging with nitrogen for 15 minutes. Sodium 4-hydroxybenzenesulfonate dihydrate (875 mg, 3.77 mmol) was dissolved in 3.6 mL 1N NaOH (3.6 mmol) and added to the reaction mixture. The reaction mixture was placed in an oil bath at 40° C. and stirred for 16 hours. The solution was dried by rotary evaporation and the product was then recrystallized from 80:20 ethanol:water. The compound was filtered then washed with ethanol and dried under vacuum at 60° C. for 18 hours.

In certain instances, a mixture of 3,3-dimethyl-2-[2-[2-chloro-3-[2-[1,3-dihydro-3,3-dimethyl-5-sulfo-1-(4-sulfobutyl)-2H-indol-2-ylidene]-ethylidene]-1-cyclohexen-1-yl]-ethenyl]-5-sulfo-1-(4-sulfobutyl)-3H-indolium hydroxide, innersalt, trisodium salt (20 g, 21 mmol) and Sodium 4-hydroxybenzenesulfonate dihydrate (5.84 g, 25.2 mmol) is suspended in water (120 ml). The suspension is heated to 85° C. where complete dissolution is observed. Aqueous sodium hydroxide (10N, 2.5 ml, 25 mmol) is added dropwise and the reaction stirred for 45 min. Isopropanol (360 ml) is added slowly to maintain the reaction temperature above 60° C. The mixture is then slowly cooled to ambient temperature and the resulting slurry filtered. The filter cake is rinsed with 40 ml isopropanol:water (3:1) and twice with 40 ml isopropanol and dried at 50-60° C. under vacuum to obtain 18.4 g of the compound of Formula 1 as a dark green solid. Ten grams (9 mmol) of this material is then recrystallized by dissolving in water (50 ml) and isopropanol (100 ml) at approximately 70° C., and slowly cooling the mixture to ambient temperature. The solids are collected by filtration and rinsed with 20 ml isopropanol: water (2:1) and twice with 20 ml isopropanol and dried at 50-60° C. under vacuum to obtain 6.7 g of the compound Formula 1 as a crystalline dark green solid.

A. Crystalline Samples for Analysis

Crystals of IRDye 800 BK were prepared via the following method: A saturated solution of IRDye 800 BK was prepared in a pre-prepared 70% 2-ethoxyethanol:30% water (v/v) solution in a 1.75 clear glass vial then capped with a pierced lid. This solution was left to stand at ambient temperature for several days without agitation to allow for the formation of exceptionally large plate-like crystals to grow that were suitable for interrogation by single crystal X-ray diffraction.

An additional crop of crystals of IRDye 800 BK was prepared via the following method: A saturated solution of IRDye 800 BK was prepared in a pre-prepared 70% 2-propanol:30% water (v/v) solution in a 1.75 clear glass vial then capped with a pierced lid. This solution was left to stand at ambient temperature for several days without agitation to allow for the formation of exceptionally large plate-like crystals to grow that were suitable for interrogation by single crystal X-ray diffraction.

B. Crystallization Development at the 300 mL Scale

The crystallization development was completed in a 300 mL CLR, using a glass 4-bladed 40 mm diameter pitch-blade impeller. The input and seed material for all 8 crystallizations was IRDye 800 BK, batch: VE-759-79-2. The batch number of starting material for crystallization 9 was C80104-01.

The first three experiments were used to determine the most promising solvent system to be used. The remaining experiments used the 2-propanol:water (50:50 v/v %) system with the seeding point (if applicable), cooling rate and anti-solvent addition point and rate all assessed as variables.

1. Crystallization 1

Crystallization 1 was carried out in the acetone:water solvent system; the following procedure was used: Approximately 10 g of IRDye 800 BK was dissolved in 50 mL acetone:water (50:50 v/v %) at 50° C. to produce a solution with a concentration of 200 mg/mL.

After a ca. 30 minute hold at 50° C., the experiment was cooled to 45° C. at a rate of 0.1° C./min before 1% seed was added. After a further 30 minute hold post-seeding, the system was cooled to 5° C. at a rate of 0.1° C./min, before holding at 5° C. for ca. 6 hours. Anti-solvent addition of acetone was then initiated at a rate of 30 mL/h, with a total of 75 mL anti-solvent added (final ratio of acetone:water was 80:20 v/v %). Samples were taken at 50%, 67%, 75% and 80% acetone content for concentration and polymorphic form analysis. Once anti-solvent addition was complete, a further 2 hour hold at 5° C. was applied, with a final slurry sample taken just before isolation. The slurry was separated through vacuum filtration, using a Buchner funnel with 70 mm diameter Whatman Grade 1 filter paper (11 µm). The mother liquor was used to wash out the vessel and then re-filtered. Once filtered, the mother liquor was analyzed for concentration and purity by HPLC. The solids were washed with 20 mL of acetone and the wash liquor was analyzed for concentration and purity by HPLC. The solid was then dried at ambient temperature under vacuum for ca. 24 hours before being analyzed by XRPD, HPLC, GC, PLM and TG/DTA. Further solid samples were dried for 48 hours and 140 hours, with the resulting solid material analyzed by XRPD, GC and TG/DTA.

2. Crystallization 2

Crystallization 2 was carried out in the ethanol:water solvent system; the following procedure was used: Approximately 9.5 g of IRDye 800 BK was dissolved in 50 mL ethanol:water (50:50 v/v %) at 50° C. to produce a solution with a concentration of 190 mg/mL. After a ca. 30 minute hold at 50° C., the experiment was cooled to 45° C. at a rate of 0.1° C./min before 1% seed was added. After a further 30 minute post-seeding hold, the system was cooled to 5° C. at a rate of 0.1° C./min before holding at 5° C. for ca. 6 hours. Anti-solvent addition of ethanol was then initiated at a rate of 30 mL/h, with a total of 75 mL anti-solvent added (final ratio of ethanol:water was 80:20 v/v %). Samples were taken at 50%, 67%, 75% and 80% ethanol content for concentration and polymorphic form analysis. Once anti-solvent addition was complete, a further 2 hour hold at 5° C. was applied, with a final slurry sample taken just before isolation. The slurry was separated through vacuum filtration, using a Buchner funnel with 70 mm diameter Whatman Grade 1 filter paper (11 µm). The mother liquor was used to wash out the vessel and then re-filtered. Once filtered, the mother liquor was analyzed for concentration and purity by HPLC. The solids were washed with 20 mL of ethanol and the wash liquor was analyzed for concentration and purity by HPLC. The solid was then dried at ambient temperature under vacuum for ca. 24 hours before being analyzed by XRPD, HPLC, GC, PLM and TG/DTA. Further solid samples were dried for 48 hours and 140 hours with the resulting solid material analyzed by XRPD, GC and TG/DTA.

3. Crystallization 3

Crystallization 3 was carried out in the 2-propanol:water solvent system; the following procedure was used: Approximately 10 g of IRDye 800 BK was dissolved in 50 mL 2-propanol:water (50:50 v/v %) at 50° C. to produce a solution with a concentration of 200 mg/mL. After a ca. 30 minute hold at 50° C., the experiment was cooled to 45° C. at a rate of 0.1° C./min before 1% seed was added. After a further 30 minute post-seeding hold, the system was cooled to 5° C. at a rate of 0.1° C./min before holding at 5° C. for ca. 6 hours. Anti-solvent addition of 2-propanol was then initiated at a rate of 30 mL/h, with a total of 75 mL anti-solvent added (final ratio of 2-propanol:water was 80:20 v/v %). Samples were taken at 50%, 67%, 75% and 80% 2-propanol content for concentration and polymorphic form analysis. Once anti-solvent addition was complete, a further 2 hour hold at 5° C. was applied, with a final slurry sample taken just before isolation. The slurry was separated through vacuum filtration, using a Buchner funnel with 70 mm diameter Whatman Grade 1 filter paper (11 µm). The mother liquor was used to wash out the vessel and then re-filtered. Once filtered, the mother liquor was analyzed for concentration and purity by HPLC. The solids were washed with 20 mL of 2-propanol and the wash liquor was analyzed for concentration and purity by HPLC. The solid was then dried at ambient temperature under vacuum for ca. 24 hours before being analyzed by XRPD, HPLC, GC, PLM and TG/DTA. Further solid samples were dried for 48 hours and 140 hours with the resulting solid material analyzed by XRPD, GC and TG/DTA.

4. Crystallization 4

Crystallization 4 was also carried out in the 2-propanol:water solvent system and varied the seed and anti-solvent addition temperature compared to Crystallization 3; the following procedure was used: Approximately 10 g of IRDye 800 BK was dissolved in 50 mL 2-propanol:water (50:50 v/v %) at 50° C. to produce a solution with a concentration of 200 mg/mL. Once fully dissolved, the solution was cooled to 40° C. at a rate of 0.1° C./min. Once at 40° C. the system was seeded with 1% IRDye 800 BK and held at this temperature for 30 minutes. Anti-solvent addition of 2-propanol was then initiated at 40° C. and a rate of 30 mL/h, with a total of 75 mL anti-solvent added (final ratio of 2-propanol:water was 80:20 v/v %). Samples were taken at 5%, 60%, 70%, 75% and 80% 2-propanol content for concentration and polymorphic form analysis. Once anti-solvent addition was complete the system was cooled to 5° C. at a rate of 0.2° C./min, before holding at 5° C. for ca. 6 hours. After the hold period a final slurry sample was taken just before isolation. The slurry was separated through vacuum filtration, using a Buchner funnel with 70 mm diameter Whatman Grade 1 filter paper (11 µm). The mother liquor was used to wash out the vessel and then re-filtered. Once filtered, the mother liquor was analyzed for concentration and purity by HPLC. The solids were washed with 20 mL of 2-propanol:water (80:20 v/v %) and the wash liquor was analyzed for concentration and purity by HPLC. The solid was then dried at ambient temperature under vacuum for ca. 100 hours before being analyzed by XRPD, HPLC, GC, PLM and TG/DTA.

5. Crystallization 5

Crystallization 5 was carried out in the 2-propanol:water solvent system without seeding. The antisolvent addition temperature was lowered compared to Crystallization 4; the following procedure was used: Ca. 10 g of IRDye 800 BK was dissolved in 50 mL 2-propanol:water (50:50 v/v %) at 50° C. to produce a solution with a concentration of 200 mg/mL. Once fully dissolved, the solution was cooled to 5° C. at a rate of 0.1° C./min and once at 5° C. held for ca. 8 hours. Anti-solvent addition of 2-propanol was then initiated at a rate of 30 mL/h, with a total of 75 mL anti-solvent added (final ratio of 2-propanol:water was 80:20 v/v %). Samples were taken at 50%, 65%, 75% and 80% 2-propanol content for concentration and polymorphic form analysis. After anti-solvent addition was complete, a further 2 hour hold at 5° C. was applied, with a final slurry sample taken just before isolation. The slurry was separated through vacuum filtration, using a Buchner funnel with 70 mm diameter Whatman Grade 1 filter paper (11 µm). The mother liquor was used to wash out the vessel and then re-filtered. Once filtered, the mother liquor was analyzed for concentration and purity by HPLC. The solids were washed with 20 mL of 2-propanol:water (80:20 v/v %) and the wash liquor was analyzed for concentration and purity by HPLC. The solid was then dried at ambient temperature under vacuum for ca. 48 hours before being analyzed by XRPD, HPLC, GC, PLM and TG/DTA. A sample of the solid was then dried further, for a total of 90 hours, before being analyzed by XRPD, HPLC, GC and TG/DTA.

6. Crystallization 6

Crystallization 6 was also carried out in the 2-propanol:water solvent system, with seed added at 40° C. The anti-solvent addition and final temperature were also changed compared to Crystallization 5; the following procedure was used: Approximately 10 g of IRDye 800 BK was dissolved in 50 mL 2-propanol:water (50:50 v/v %) at 50° C. to produce a solution with a concentration of 200 mg/mL. Once fully dissolved, the solution was cooled to 40° C. at a rate of 0.1° C./min, before being seeded with 1% seed and held at this temperature for 30 minutes. The system was then cooled to 25° C. at a rate of 0.1° C./min. Once at 25° C., anti-solvent addition of 2-propanol was initiated at a rate of 30 mL/h, with a total of 75 mL anti-solvent added (final ratio of 2-propanol:water was 80:20 v/v %). Samples were taken at 50%, 65%, 75% and 80% 2-propanol content for concentration and polymorphic form analysis. After anti-solvent addition was complete, a further 18 hour hold at 25° C. was carried out, with a final slurry sample taken just before isolation. The slurry was separated through vacuum filtration, using a Buchner funnel with 70 mm diameter Whatman Grade 1 filter paper (11 μm). The mother liquor was used to wash out the vessel and then re-filtered. Once filtered, the mother liquor was analyzed for concentration and purity by HPLC. The solids were washed with 20 mL of 2-propanol:water (80:20 v/v %) and the wash liquor was analyzed for concentration and purity by HPLC. The solid was then dried at ambient temperature under vacuum for ca. 24 hours before being nalyzed by XRPD, HPLC, GC, PLM and TG/DTA. A sample of the solid was then dried further, for a total of 80 hours, before being analyzed by XRPD, HPLC, GC, PLM and TG/DTA.

7. Crystallization 7

Crystallization 7 was carried out in the 2-propanol:water solvent system, altering the anti-solvent volume and addition rate, along with the final system temperature compared to Crystallization 6; the following procedure was used: Approximately 10 g of IRDye 800 BK was dissolved in 50 mL 2-propanol:water (50:50 v/v %) at 50° C. to produce a solution with a concentration of 200 mg/mL. Once fully dissolved, the solution was cooled to 20° C. at a rate of 0.1° C./min. Once at 20° C., anti-solvent addition of 2-propanol was then initiated at a rate of 20 mL/h, with a total of 50 mL anti-solvent added (final ratio of 2-propanol:water was 75:25 v/v %). Samples were taken at 50%, 60%, 70% and 75% 2-propanol content for concentration and polymorphic form analysis. After anti-solvent addition was complete, a further 18 hour hold at 20° C. was applied, with a final slurry sample taken just before isolation. The slurry was separated through vacuum filtration, using a Buchner funnel with 70 mm diameter Whatman Grade 1 filter paper (11 μm). The mother liquor was used to wash out the vessel and then re-filtered. Once filtered, the mother liquor was analyzed for concentration and purity by HPLC. The solids were washed with 20 mL of 2-propanol:water (80:20 v/v %), the wash liquor was analyzed for concentration and purity by HPLC. The solid was then dried at ambient temperature under vacuum for ca. 24 hours before being analyzed by XRPD, HPLC, GC, PLM and TG/DTA. A sample of the solid was then dried further, for a total of 80 hours, before being analyzed by XRPD, HPLC, GC, PLM and TG/DTA.

8. Crystallization 8

Crystallization 8 was also carried out in the 2-propanol:water solvent system with an altered cooling rate used compared to Crystallization 7; the following procedure was used: Approximately 10 g of IRDye 800 BK was dissolved in 50 mL 2-propanol:water (50:50 v/v %) at 50° C. to produce a solution with a concentration of 200 mg/mL. Once fully dissolved, the solution was cooled to 20° C. at a rate of 0.05° C./min. Once at 20° C., anti-solvent addition of 2-propanol was initiated at a rate of 20 mL/h, with a total of 50 mL anti-solvent added (final ratio of 2-propanol:water was 75:25 v/v %). Once anti-solvent addition was complete, a further 2 hour hold at 20° C. was applied with a slurry sample taken just before isolation. The slurry was separated through vacuum filtration, using a Buchner funnel with 70 mm diameter Whatman Grade 1 filter paper (11 μm). The mother liquor was used to wash out the vessel and then re-filtered. Once filtered, the mother liquor was analyzed for concentration and purity by HPLC. The solids were washed with 20 mL of 2-propanol:water (80:20 v/v %) and the wash liquor was analyzed for concentration and purity by HPLC. The solid was then dried at ambient temperature under vacuum for ca. 48 hours before being analyzed by XRPD, HPLC, GC, PLM and TG/DTA. A sample of the solid was then dried further, for a total of 140 hours, before being analyzed by XRPD, HPLC, GC, PLM and TG/DTA.

9. Crystallization 9

Crystallization 9 was carried out in the 2-propanol:water solvent system with an altered volumes of water and 2-propanol used compared to Crystallization 8; the following procedure was used: Approximately 10 g of IRDye 800 BK was dissolved in 50 mL water to produce a solution with a concentration of 200 mg/mL. Filter this solution and add 150 ml 2-propanol dropwise in to the solution to obtain a slurry (final ratio of 2-propanol:water was 75:25 v/v %).

This slurry is then heated to 70° C. and hold it at 70° C. for 5 mins. The solution was then cooled to 25° C. The slurry was separated through vacuum filtration, using a Buchner funnel with 70 mm diameter Whatman Grade 1 filter paper (11 Om). 28 mL of 2-propanol:water (75:25 v/v %) was used to wash out the vessel and then re-filtered. Once filtered, the mother liquor was analyzed for concentration and purity by HPLC using method 2. The solids were washed with (2) 10 ml 2-propanol and the wash liquor was analyzed for concentration and purity by HPLC. The solid was then dried at ambient temperature under vacuum for ca. 4 hours before being analyzed by XRPD and HPLC.

Example 2: X-Ray Powder Diffraction (XRPD) XRPD Analysis was Carried Out on a Panalytical X'pert pro, scanning the samples between 3 and 35° 2θ. The material was gently ground and loaded onto a multiwell plate with Kapton or mylar polymer film to support the sample. XRPD analysis was carried out on a Panalytical X'pert pro, scanning the samples between 3 and 35° 2θ. The material was gently ground and loaded onto a multi well plate with Kapton or mylar polymer film to support the sample. The multi well plate was then loaded into a Panalytical diffractometer running in transmission mode and analysed, using the following experimental conditions.

| Raw Data Origin: | XRD measurement (*.XRDML) |
|---|---|
| Scan Axis: | Gonio |
| Start Position [°2θ]: | 3.0066 |
| End Position [°2θ]: | 34.9866 |
| Step Size [°2θ]: | 0.0130 |
| Scan Step Time [s]: | 18.8700 |
| Scan Type: | Continuous |
| PSD Mode: | Scanning |
| PSD Length [°2θ]: | 3.35 |
| Offset [°2θ]: | 0.0000 |
| Divergence Slit Type: | Fixed |
| Divergence Slit Size [°]: | 1.0000 |
| Measurement Temperature [° C.]: | 25.00 |
| Anode Material: | Cu |
| K-Alpha1 [Å]: | 1.54060 |
| K-Alpha2 [Å]: | 1.54443 |
| K-Beta [Å]: | 1.39225 |
| K-A2/K-A1 Ratio: | 0.50000 |
| Generator Settings: | 40 mA, 40 kV |
| Goniometer Radius [mm]: | 240.00 |
| Dist. Focus-Diverg. Slit [mm]: | 91.00 |
| Incident Beam Monochromator: | No |
| Spinning: | No |

The multiwell plate was then loaded into a Panalytical diffractometer running in transmission mode and analyzed. The results are shown in in FIGS. 1-15, with tabulated peak heights listed in Tables 1-15.

IRDye 800 BK, Pattern 1

TABLE 1A

XRPD peak table for IRDye 800BK (lot# Lot VE759-42-1), pattern 1.

| Pos. [°2Th.] ± 0.2 | FWHM [°2Th.] | Area [cts * °2Th.] | Backgr. [cts] | d-spacing [Å] | Height [cts] | Rel. Int. [%] |
|---|---|---|---|---|---|---|
| 4.2561 | 0.0355 | 48.94 | 427.88 | 20.7617 | 717.29 | 100.00 |
| 5.2537 | 0.1421 | 55.50 | 361.15 | 16.8214 | 203.38 | 28.35 |
| 9.6141 | 0.0533 | 39.85 | 220.00 | 9.1996 | 389.39 | 54.29 |
| 10.5626 | 0.1066 | 37.86 | 244.00 | 8.3756 | 184.96 | 25.79 |
| 12.8879 | 0.0711 | 62.78 | 280.00 | 6.8692 | 460.08 | 64.14 |
| 13.3861 | 0.0993 | 50.21 | 279.00 | 6.6146 | 263.30 | 36.71 |
| 14.0040 | 0.0709 | 30.13 | 272.05 | 6.3242 | 221.28 | 30.85 |
| 14.2270 | 0.1066 | 42.47 | 268.00 | 6.2255 | 207.52 | 28.93 |
| 15.0778 | 0.1066 | 31.32 | 264.56 | 5.8761 | 153.05 | 21.34 |
| 15.4332 | 0.0860 | 49.37 | 269.00 | 5.7415 | 298.99 | 41.68 |
| 15.8690 | 0.0711 | 49.32 | 272.00 | 5.5848 | 361.48 | 50.39 |
| 16.2937 | 0.0877 | 55.39 | 271.00 | 5.4402 | 328.80 | 45.84 |
| 16.7346 | 0.0069 | 2.85 | 267.00 | 5.2979 | 213.62 | 29.78 |
| 17.2909 | 0.1066 | 34.31 | 277.79 | 5.1287 | 167.62 | 23.37 |
| 17.9956 | 0.0069 | 4.78 | 298.00 | 4.9294 | 358.74 | 50.01 |
| 18.2819 | 0.1066 | 60.22 | 303.00 | 4.8528 | 294.21 | 41.02 |
| 18.7236 | 0.0069 | 6.80 | 307.00 | 4.7393 | 510.24 | 71.13 |
| 19.1021 | 0.1066 | 47.41 | 308.00 | 4.6463 | 231.64 | 32.29 |
| 19.6777 | 0.1066 | 40.49 | 305.00 | 4.5116 | 197.83 | 27.58 |
| 20.1543 | 0.0888 | 36.61 | 304.00 | 4.4060 | 214.66 | 29.93 |
| 20.4748 | 0.1312 | 101.11 | 302.29 | 4.3378 | 401.40 | 55.96 |
| 20.7367 | 0.1066 | 116.32 | 300.00 | 4.2836 | 568.35 | 79.23 |
| 21.2387 | 0.1244 | 98.62 | 293.00 | 4.1834 | 413.03 | 57.58 |
| 21.7380 | 0.1066 | 30.22 | 284.00 | 4.0885 | 147.63 | 20.58 |
| 22.5592 | 0.2132 | 71.40 | 263.95 | 3.9415 | 174.42 | 24.32 |
| 23.3950 | 0.2843 | 68.28 | 249.00 | 3.8025 | 125.11 | 17.44 |
| 26.3608 | 0.1421 | 32.96 | 210.52 | 3.3810 | 120.78 | 16.84 |
| 28.5984 | 0.1421 | 27.05 | 196.00 | 3.1214 | 99.13 | 13.82 |

IRDye 800 BK, Pattern 1

TABLE 1B

XRPD peak table for IRDye 800 BK, pattern 1
Table - IRDye 800BK (Batch: RP-794-66)

| No. | Pos. [°2θ] | d-spacing [Å] | Height [cts] | Backgr. [cts] | Area [cts * 2θ 2θ] | Rel. Int. [%] |
|---|---|---|---|---|---|---|
| 1 | 4.29 | 20.61 | 990.21 | 232.70 | 49.98 | 100.00 |
| 2 | 4.78 | 18.47 | 155.72 | 217.85 | 11.79 | 15.73 |
| 3 | 5.46 | 16.17 | 170.88 | 197.28 | 8.63 | 17.26 |
| 4 | 6.30 | 14.03 | 80.66 | 164.15 | 24.43 | 8.15 |
| 5 | 7.01 | 12.61 | 23.08 | 136.27 | 1.85 | 2.33 |
| 6 | 7.38 | 11.97 | 74.35 | 130.75 | 11.26 | 7.51 |
| 7 | 8.52 | 10.37 | 56.22 | 130.69 | 8.51 | 5.68 |
| 8 | 8.97 | 9.85 | 54.22 | 131.95 | 4.34 | 5.48 |
| 9 | 9.60 | 9.21 | 503.16 | 133.72 | 44.44 | 50.81 |
| 10 | 10.56 | 8.38 | 185.62 | 136.42 | 23.42 | 18.75 |
| 11 | 10.83 | 8.17 | 187.93 | 137.17 | 14.23 | 18.98 |
| 12 | 11.54 | 7.67 | 114.00 | 139.18 | 34.52 | 11.51 |
| 13 | 12.73 | 6.96 | 419.81 | 142.51 | 31.78 | 42.40 |
| 14 | 12.93 | 6.85 | 591.49 | 143.07 | 29.86 | 59.73 |
| 15 | 13.50 | 6.56 | 153.12 | 144.69 | 30.91 | 15.46 |
| 16 | 13.89 | 6.38 | 63.09 | 145.79 | 9.55 | 6.37 |
| 17 | 14.56 | 6.08 | 193.80 | 147.67 | 19.56 | 19.57 |
| 18 | 14.85 | 5.97 | 185.14 | 148.49 | 18.69 | 18.70 |
| 19 | 15.46 | 5.73 | 211.41 | 152.27 | 18.67 | 21.35 |
| 20 | 15.90 | 5.57 | 320.86 | 155.63 | 32.39 | 32.40 |
| 21 | 16.12 | 5.50 | 305.39 | 157.27 | 30.83 | 30.84 |
| 22 | 16.42 | 5.40 | 207.46 | 159.55 | 26.18 | 20.95 |
| 23 | 16.84 | 5.26 | 169.74 | 162.76 | 25.70 | 17.14 |
| 24 | 17.61 | 5.04 | 192.16 | 168.60 | 14.55 | 19.41 |
| 25 | 18.02 | 4.92 | 314.52 | 171.74 | 35.72 | 31.76 |
| 26 | 18.30 | 4.85 | 411.72 | 173.87 | 51.95 | 41.58 |
| 27 | 18.74 | 4.73 | 394.01 | 177.22 | 59.66 | 39.79 |
| 28 | 19.14 | 4.64 | 416.65 | 180.27 | 63.09 | 42.08 |
| 29 | 19.76 | 4.49 | 412.98 | 184.99 | 62.54 | 41.71 |

TABLE 1B-continued

XRPD peak table for IRDye 800 BK, pattern 1
Table - IRDye 800BK (Batch: RP-794-66)

| No. | Pos. [°2θ] | d-spacing [Å] | Height [cts] | Backgr. [cts] | Area [cts * 2θ 2θ] | Rel. Int. [%] |
|---|---|---|---|---|---|---|
| 30 | 20.21 | 4.39 | 411.43 | 188.37 | 51.92 | 41.55 |
| 31 | 20.51 | 4.33 | 420.34 | 190.64 | 42.43 | 42.45 |
| 32 | 20.80 | 4.27 | 550.08 | 192.89 | 69.41 | 55.55 |
| 33 | 21.10 | 4.21 | 670.39 | 195.19 | 67.68 | 67.70 |
| 34 | 21.30 | 4.17 | 516.63 | 196.66 | 78.23 | 52.17 |
| 35 | 21.76 | 4.08 | 292.14 | 200.20 | 29.49 | 29.50 |
| 36 | 22.55 | 3.94 | 243.65 | 206.14 | 61.49 | 24.61 |
| 37 | 23.40 | 3.80 | 156.55 | 207.55 | 47.41 | 15.81 |
| 38 | 24.03 | 3.70 | 22.01 | 203.21 | 1.76 | 2.22 |
| 39 | 24.61 | 3.62 | 90.28 | 199.12 | 13.67 | 9.12 |
| 40 | 25.23 | 3.53 | 148.17 | 194.81 | 26.18 | 14.96 |
| 41 | 26.30 | 3.39 | 191.16 | 187.36 | 28.95 | 19.31 |
| 42 | 28.08 | 3.18 | 100.75 | 174.96 | 15.26 | 10.17 |
| 43 | 28.66 | 3.11 | 129.30 | 170.93 | 19.58 | 13.06 |
| 44 | 29.25 | 3.05 | 95.38 | 166.84 | 28.89 | 9.63 |
| 45 | 30.05 | 2.97 | 45.98 | 161.29 | 3.68 | 4.64 |
| 46 | 31.10 | 2.88 | 64.97 | 162.07 | 39.35 | 6.56 |
| 47 | 32.46 | 2.76 | 62.21 | 168.31 | 25.12 | 6.28 |

IRDye 800 BK, Pattern 2

TABLE 2

XRPD peak table for IRDye 800 BK, pattern 2.

| Pos. [°2Th.] ± 0.2 | FWHM [°2Th.] | Area [cts*°2Th.] | Backgr. [cts] | d-spacing [Å] | Height [cts] | Rel. Int. [%] |
|---|---|---|---|---|---|---|
| 4.6945 | 0.3070 | 38.90 | 402.16 | 18.8235 | 128.43 | 15.44 |
| 9.4796 | 0.1535 | 27.39 | 230.00 | 9.3299 | 180.87 | 21.74 |
| 11.5447 | 0.1313 | 16.87 | 270.00 | 7.6652 | 192.75 | 23.17 |
| 12.4277 | 0.0990 | 13.33 | 295.00 | 7.1225 | 201.98 | 24.28 |
| 13.0283 | 0.1329 | 20.39 | 305.00 | 6.7955 | 230.04 | 27.66 |
| 13.7940 | 0.1052 | 11.07 | 306.00 | 6.4200 | 157.87 | 18.98 |
| 14.7884 | 0.1279 | 21.67 | 293.00 | 5.9994 | 171.70 | 20.64 |
| 15.9645 | 0.3522 | 45.94 | 287.00 | 5.5517 | 195.61 | 23.52 |
| 16.0326 | 0.0100 | 1.66 | 287.00 | 5.5282 | 248.39 | 29.86 |
| 16.4226 | 0.2115 | 29.39 | 285.00 | 5.3978 | 208.45 | 25.06 |
| 16.9083 | 0.2047 | 34.71 | 279.00 | 5.2438 | 171.94 | 20.67 |
| 17.3196 | 0.0100 | 0.93 | 269.00 | 5.1202 | 139.22 | 16.74 |
| 19.1471 | 0.1535 | 44.66 | 275.58 | 4.6354 | 294.94 | 35.46 |
| 19.5358 | 0.1791 | 50.09 | 284.00 | 4.5441 | 283.54 | 34.09 |
| 19.8242 | 0.1535 | 51.25 | 288.00 | 4.4786 | 338.48 | 40.69 |
| 20.5790 | 0.1535 | 35.55 | 290.00 | 4.3160 | 234.76 | 28.22 |
| 21.0201 | 0.0895 | 73.47 | 284.00 | 4.2265 | 831.80 | 100.00 |
| 21.3092 | 0.3600 | 113.27 | 278.00 | 4.1698 | 472.03 | 56.75 |
| 21.9298 | 0.0792 | 11.19 | 260.36 | 4.0531 | 211.83 | 25.47 |
| 22.3835 | 0.1535 | 24.75 | 243.00 | 3.9720 | 163.46 | 19.65 |
| 26.2427 | 0.3070 | 29.11 | 175.00 | 3.3960 | 96.11 | 11.55 |

IRDye 800 BK, Pattern 3

TABLE 3

XRPD peak table for IRDye 800 BK, pattern 3.

| Pos. [°2Th.] ± 0.2 | FWHM [°2Th.] | Area [cts*°2Th.] | Backgr. [cts] | d-spacing [Å] | Height [cts] | Rel. Int. [%] |
|---|---|---|---|---|---|---|
| 5.4582 | 0.1023 | 36.97 | 398.41 | 16.1914 | 366.18 | 100.00 |
| 6.7753 | 0.1288 | 16.71 | 323.00 | 13.0466 | 194.58 | 53.14 |
| 7.4887 | 0.3070 | 25.24 | 308.00 | 11.8052 | 83.33 | 22.76 |
| 8.9758 | 0.1732 | 22.30 | 286.00 | 9.8524 | 193.12 | 52.74 |
| 10.4620 | 0.3070 | 21.37 | 319.00 | 8.4559 | 70.56 | 19.27 |
| 11.0554 | 0.2024 | 24.72 | 338.00 | 8.0033 | 183.23 | 50.04 |
| 13.4459 | 0.2508 | 16.21 | 366.00 | 6.5853 | 96.94 | 26.47 |
| 15.5042 | 0.2090 | 25.48 | 350.00 | 5.7154 | 182.88 | 49.94 |
| 16.1900 | 0.4093 | 40.75 | 331.89 | 5.4748 | 100.92 | 27.56 |
| 18.0678 | 0.1087 | 13.81 | 304.00 | 4.9098 | 190.65 | 52.07 |
| 20.7126 | 0.4093 | 31.12 | 271.00 | 4.2885 | 77.07 | 21.05 |
| 22.3811 | 0.8187 | 48.20 | 248.00 | 3.9724 | 59.68 | 16.30 |

IRDye 800 BK, Pattern 4

TABLE 4

XRPD peak table for IRDye 800 BK, pattern 4.

| Pos. [°2Th.] ± 0.2 | FWHM [°2Th.] | Area [cts*°2Th.] | Backgr. [cts] | d-spacing [Å] | Height [cts] | Rel. Int. [%] |
|---|---|---|---|---|---|---|
| 4.6095 | 0.0768 | 58.45 | 359.70 | 19.1706 | 772.00 | 100.00 |
| 5.4112 | 0.1535 | 31.21 | 319.03 | 16.3320 | 206.14 | 26.70 |
| 5.9706 | 0.3218 | 106.13 | 284.00 | 14.8031 | 494.66 | 64.07 |
| 6.1473 | 0.0640 | 37.23 | 272.41 | 14.3779 | 590.01 | 76.43 |
| 8.0354 | 0.1535 | 20.00 | 211.00 | 11.0033 | 132.05 | 17.11 |
| 9.3896 | 0.0900 | 5.98 | 189.00 | 9.4192 | 99.69 | 12.91 |
| 10.7526 | 0.6140 | 50.03 | 241.85 | 8.2280 | 82.60 | 10.70 |
| 11.9990 | 0.1062 | 26.35 | 290.00 | 7.3760 | 372.27 | 48.22 |
| 12.4243 | 0.2303 | 102.36 | 299.00 | 7.1245 | 450.67 | 58.38 |
| 12.9722 | 0.2067 | 29.81 | 306.00 | 6.8248 | 216.32 | 28.02 |
| 13.3613 | 0.6140 | 57.58 | 307.00 | 6.6268 | 95.06 | 12.31 |
| 14.2590 | 0.0360 | 4.09 | 305.00 | 6.2116 | 170.57 | 22.09 |
| 15.4614 | 0.2442 | 48.80 | 335.07 | 5.7311 | 299.74 | 38.83 |
| 15.9007 | 0.2262 | 60.24 | 346.00 | 5.5738 | 399.48 | 51.75 |
| 16.4064 | 0.2047 | 112.13 | 354.00 | 5.4031 | 555.39 | 71.94 |
| 17.3938 | 0.1535 | 29.59 | 358.00 | 5.0985 | 195.43 | 25.31 |
| 17.6530 | 0.1042 | 20.23 | 356.00 | 5.0243 | 291.11 | 37.71 |
| 18.5606 | 0.1279 | 44.84 | 349.00 | 4.7806 | 355.36 | 46.03 |
| 18.9192 | 0.1023 | 54.02 | 347.00 | 4.6908 | 535.16 | 69.32 |
| 19.2943 | 0.1279 | 63.68 | 342.00 | 4.6004 | 504.69 | 65.37 |
| 19.8162 | 0.2047 | 24.42 | 331.00 | 4.4804 | 120.97 | 15.67 |
| 20.4115 | 0.1535 | 66.92 | 332.00 | 4.3511 | 441.96 | 57.25 |
| 20.8179 | 0.0514 | 11.07 | 337.00 | 4.2670 | 322.68 | 41.80 |
| 22.5029 | 0.3070 | 33.19 | 357.00 | 3.9512 | 109.59 | 14.20 |
| 23.2661 | 0.2142 | 28.09 | 358.00 | 3.8233 | 196.72 | 25.48 |
| 23.9890 | 0.0608 | 7.71 | 349.00 | 3.7097 | 190.33 | 24.65 |
| 25.0851 | 0.0853 | 11.09 | 314.00 | 3.5500 | 194.97 | 25.26 |
| 25.9631 | 0.0459 | 7.68 | 296.00 | 3.4319 | 251.38 | 32.56 |
| 26.9866 | 0.6140 | 60.29 | 281.39 | 3.3041 | 99.53 | 12.89 |

IRDye 800 BK, Pattern 5

TABLE 5

XRPD peak table for IRDye 800 BK, pattern 5.

| Pos. [°2Th.] ± 0.2 | FWHM [°2Th.] | Area [cts*°2Th.] | Backgr. [cts] | d-spacing [Å] | Height [cts] | Rel. Int. [%] |
|---|---|---|---|---|---|---|
| 5.0928 | 0.3025 | 106.33 | 364.00 | 17.3522 | 527.36 | 99.10 |
| 5.3751 | 0.1791 | 94.01 | 347.81 | 16.4418 | 532.13 | 100.00 |
| 6.8474 | 0.1279 | 25.42 | 277.00 | 12.9093 | 201.44 | 37.85 |
| 7.1146 | 0.1373 | 25.34 | 268.00 | 12.4252 | 276.84 | 52.02 |
| 7.4244 | 0.2047 | 31.95 | 256.00 | 11.9073 | 158.25 | 29.74 |
| 10.5147 | 0.1535 | 15.52 | 244.55 | 8.4137 | 102.51 | 19.26 |
| 10.9028 | 0.1535 | 12.96 | 255.00 | 8.1150 | 85.56 | 16.08 |
| 13.7523 | 0.1646 | 16.03 | 319.00 | 6.4393 | 146.10 | 27.46 |
| 15.7160 | 0.2047 | 25.83 | 328.00 | 5.6389 | 127.92 | 24.04 |
| 17.3444 | 0.2966 | 34.54 | 309.00 | 5.1130 | 174.66 | 32.82 |
| 17.8384 | 0.9210 | 90.49 | 313.00 | 4.9725 | 99.60 | 18.72 |
| 19.2858 | 0.2018 | 21.68 | 321.00 | 4.6024 | 161.12 | 30.28 |
| 19.9966 | 0.1535 | 16.26 | 322.00 | 4.4404 | 107.38 | 20.18 |
| 20.6228 | 0.6140 | 38.11 | 316.00 | 4.3070 | 62.92 | 11.82 |
| 22.0989 | 0.7164 | 49.28 | 300.36 | 4.0225 | 69.73 | 13.10 |
| 25.1760 | 0.3070 | 18.57 | 275.00 | 3.5374 | 61.32 | 11.52 |

IRDye 800 BK, Pattern 6

TABLE 6

XRPD peak table for IRDye 800 BK, pattern 6.

| Pos. [°2Th.] ± 0.2 | FWHM [°2Th.] | Area [cts*°2Th.] | Backgr. [cts] | d-spacing [Å] | Height [cts] | Rel. Int. [%] |
|---|---|---|---|---|---|---|
| 4.0156 | 0.1535 | 12.46 | 427.38 | 22.0045 | 82.27 | 24.72 |
| 4.4420 | 0.4093 | 35.77 | 397.58 | 19.8929 | 88.59 | 26.62 |
| 4.7214 | 0.0768 | 24.38 | 377.09 | 18.7165 | 321.99 | 96.75 |
| 5.6359 | 0.0512 | 15.56 | 328.00 | 15.6813 | 308.25 | 92.63 |
| 5.9876 | 0.0564 | 6.25 | 313.00 | 14.7610 | 166.27 | 49.96 |
| 6.4220 | 0.0768 | 20.06 | 293.00 | 13.7635 | 264.94 | 79.61 |
| 8.1918 | 0.0768 | 8.36 | 237.00 | 10.7935 | 110.45 | 33.19 |
| 9.4625 | 0.1535 | 7.66 | 219.00 | 9.3468 | 50.58 | 15.20 |
| 10.4036 | 0.0900 | 2.62 | 240.00 | 8.5033 | 43.67 | 13.12 |
| 10.7093 | 0.0768 | 22.79 | 252.52 | 8.2612 | 301.05 | 90.46 |
| 11.8430 | 0.0640 | 21.00 | 285.73 | 7.4728 | 332.79 | 100.00 |
| 12.1366 | 0.0169 | 2.11 | 291.00 | 7.2927 | 187.77 | 56.42 |
| 12.6958 | 0.3440 | 40.58 | 298.00 | 6.9727 | 176.94 | 53.17 |
| 12.8843 | 0.0768 | 16.07 | 299.00 | 6.8711 | 212.27 | 63.79 |
| 13.0863 | 0.0703 | 10.30 | 300.00 | 6.7655 | 219.74 | 66.03 |
| 13.5161 | 0.1179 | 10.98 | 301.00 | 6.5513 | 139.80 | 42.01 |
| 14.7468 | 0.0768 | 11.13 | 291.00 | 6.0072 | 147.04 | 44.18 |
| 15.5971 | 0.0431 | 4.37 | 286.00 | 5.6816 | 152.09 | 45.70 |
| 16.0326 | 0.2025 | 17.25 | 286.00 | 5.5282 | 127.77 | 38.39 |
| 16.5025 | 0.1023 | 21.94 | 284.00 | 5.3719 | 217.33 | 65.31 |
| 17.1609 | 0.0768 | 23.29 | 276.21 | 5.1672 | 307.64 | 92.44 |
| 18.1502 | 0.1151 | 23.47 | 276.00 | 4.8878 | 206.70 | 62.11 |
| 18.6188 | 0.1023 | 14.65 | 277.00 | 4.7658 | 145.17 | 43.62 |
| 19.0356 | 0.0100 | 1.11 | 275.00 | 4.6624 | 166.92 | 50.16 |
| 19.5932 | 0.1535 | 37.38 | 269.00 | 4.5309 | 246.84 | 74.17 |
| 20.3571 | 0.1535 | 23.26 | 254.34 | 4.3626 | 153.64 | 46.17 |
| 21.0271 | 0.2558 | 35.78 | 250.00 | 4.2250 | 141.77 | 42.60 |
| 21.5103 | 0.1279 | 24.40 | 253.00 | 4.1312 | 193.38 | 58.11 |
| 22.0856 | 0.4093 | 97.05 | 253.00 | 4.0249 | 240.35 | 72.22 |
| 22.9795 | 0.5117 | 59.35 | 245.00 | 3.8703 | 117.59 | 35.33 |
| 23.9034 | 0.1535 | 14.24 | 230.00 | 3.7228 | 94.02 | 28.25 |
| 24.2226 | 0.4093 | 15.86 | 226.00 | 3.6744 | 39.29 | 11.81 |
| 25.4245 | 0.1279 | 13.41 | 210.00 | 3.5034 | 106.29 | 31.94 |
| 25.9565 | 0.1535 | 15.98 | 204.00 | 3.4328 | 105.54 | 31.71 |
| 26.9000 | 0.1535 | 15.18 | 186.00 | 3.3144 | 100.22 | 30.12 |
| 27.2646 | 0.0900 | 4.75 | 176.00 | 3.2710 | 79.12 | 23.79 |
| 27.9413 | 0.2558 | 17.83 | 167.00 | 3.1933 | 70.67 | 21.24 |
| 28.4476 | 0.0900 | 4.23 | 165.00 | 3.1376 | 70.55 | 21.20 |
| 31.9790 | 0.1535 | 6.77 | 141.00 | 2.7987 | 44.71 | 13.44 |

IRDye 800 BK, Pattern 7 IRDye 800 BK, Pattern 7—Example 1

TABLE 7

XRPD peak table for IRDye 800 BK, pattern 7 (example #1).

| Pos. [°2Th.] ± 0.2 | FWHM [°2Th.] | Area [cts*°2Th.] | Backgr. [cts] | d-spacing [Å] | Height [cts] | Rel. Int. [%] |
|---|---|---|---|---|---|---|
| 4.7572 | 0.0768 | 28.82 | 351.34 | 18.5758 | 380.71 | 33.13 |
| 5.1882 | 0.0768 | 13.71 | 335.00 | 17.0333 | 181.09 | 15.76 |
| 5.9858 | 0.0512 | 21.69 | 290.00 | 14.7654 | 429.74 | 37.40 |
| 6.4068 | 0.1023 | 21.30 | 258.89 | 13.7962 | 211.03 | 18.37 |
| 9.5608 | 0.0768 | 21.64 | 220.00 | 9.2508 | 285.85 | 24.88 |
| 9.7148 | 0.0640 | 25.67 | 226.00 | 9.1045 | 406.86 | 35.41 |
| 10.5338 | 0.0768 | 9.54 | 259.02 | 8.3984 | 126.00 | 10.97 |
| 11.0772 | 0.0352 | 6.27 | 281.00 | 7.9877 | 267.66 | 23.30 |
| 11.3208 | 0.1422 | 26.34 | 290.56 | 7.8163 | 277.93 | 24.19 |
| 11.5474 | 0.1023 | 29.10 | 298.00 | 7.6634 | 288.23 | 25.09 |
| 11.9862 | 0.0640 | 38.77 | 316.00 | 7.3838 | 614.48 | 53.48 |
| 12.4357 | 0.0768 | 12.91 | 335.00 | 7.1179 | 170.55 | 14.84 |
| 12.8832 | 0.0768 | 34.52 | 347.00 | 6.8717 | 455.99 | 39.69 |
| 13.0822 | 0.1023 | 40.73 | 351.00 | 6.7676 | 403.50 | 35.12 |
| 14.2259 | 0.0895 | 25.95 | 351.97 | 6.2260 | 293.81 | 25.57 |
| 14.8004 | 0.0768 | 36.70 | 337.00 | 5.9856 | 484.71 | 42.19 |
| 15.6395 | 0.1447 | 34.21 | 353.00 | 5.6663 | 354.50 | 30.85 |
| 15.8412 | 0.1023 | 22.90 | 360.00 | 5.5946 | 226.84 | 19.74 |
| 16.0836 | 0.0656 | 11.50 | 366.00 | 5.5108 | 263.20 | 22.91 |
| 16.3956 | 0.1023 | 26.82 | 371.00 | 5.4066 | 265.72 | 23.13 |
| 16.6274 | 0.0895 | 42.02 | 373.00 | 5.3318 | 475.69 | 41.40 |
| 16.8640 | 0.0895 | 20.32 | 373.00 | 5.2575 | 230.05 | 20.02 |
| 17.4168 | 0.2047 | 73.71 | 369.00 | 5.0919 | 365.10 | 31.78 |
| 18.0437 | 0.1535 | 19.42 | 371.00 | 4.9164 | 128.26 | 11.16 |
| 18.4298 | 0.1279 | 20.66 | 381.40 | 4.8142 | 163.75 | 14.25 |
| 19.0226 | 0.2047 | 46.08 | 406.00 | 4.6655 | 228.24 | 19.86 |
| 19.1828 | 0.0768 | 21.21 | 413.00 | 4.6269 | 280.20 | 24.39 |
| 19.5683 | 0.1023 | 32.29 | 426.00 | 4.5366 | 319.88 | 27.84 |
| 19.8552 | 0.1023 | 37.22 | 433.05 | 4.4717 | 368.72 | 32.09 |
| 20.2384 | 0.0895 | 16.89 | 438.00 | 4.3879 | 191.25 | 16.65 |
| 20.6379 | 0.1279 | 50.11 | 439.00 | 4.3039 | 397.12 | 34.56 |
| 21.0470 | 0.0768 | 75.89 | 434.27 | 4.2211 | 1002.29 | 87.23 |
| 21.1726 | 0.1151 | 130.49 | 433.00 | 4.1964 | 1148.99 | 100.00 |
| 21.9262 | 0.0895 | 25.13 | 411.64 | 4.0538 | 284.52 | 24.76 |
| 22.4380 | 0.1791 | 40.07 | 387.00 | 3.9625 | 226.81 | 19.74 |
| 23.1762 | 0.1023 | 18.69 | 359.51 | 3.8379 | 185.11 | 16.11 |
| 23.6305 | 0.1279 | 21.78 | 361.00 | 3.7651 | 172.58 | 15.02 |
| 25.1091 | 0.2047 | 40.07 | 357.00 | 3.5467 | 198.45 | 17.27 |
| 26.2012 | 0.2303 | 78.07 | 342.00 | 3.4013 | 343.72 | 29.92 |
| 27.6932 | 0.1279 | 23.10 | 295.00 | 3.2213 | 183.05 | 15.93 |

IRDye 800 BK Pattern 7—Example 2

TABLE 8

XRPD peak table for IRDye 800 BK, pattern 7 (example #2).

| Pos. [°2Th.] ± 0.2 | FWHM [°2Th.] | Area [cts*°2Th.] | Backgr. [cts] | d-spacing [Å] | Height [cts] | Rel. Int. [%] |
|---|---|---|---|---|---|---|
| 4.2407 | 0.0768 | 9.80 | 384.00 | 20.8369 | 129.45 | 17.12 |
| 4.7474 | 0.1023 | 28.75 | 359.09 | 18.6139 | 284.81 | 37.67 |
| 5.2269 | 0.2047 | 21.03 | 337.20 | 16.9074 | 104.14 | 13.78 |
| 5.9849 | 0.0768 | 12.70 | 297.00 | 14.7677 | 167.76 | 22.19 |
| 6.3976 | 0.1023 | 13.50 | 272.00 | 13.8158 | 133.69 | 17.68 |
| 9.5680 | 0.0907 | 29.85 | 222.00 | 9.2439 | 493.52 | 65.28 |
| 9.6947 | 0.0768 | 21.57 | 224.47 | 9.1234 | 284.90 | 37.69 |
| 10.5482 | 0.1535 | 12.30 | 261.12 | 8.3870 | 81.25 | 10.75 |
| 11.0493 | 0.0672 | 9.66 | 290.00 | 8.0077 | 215.73 | 28.54 |
| 11.5389 | 0.1279 | 24.70 | 313.33 | 7.6691 | 195.76 | 25.89 |
| 11.9978 | 0.1279 | 14.35 | 332.00 | 7.3767 | 113.75 | 15.05 |
| 12.8775 | 0.1279 | 38.04 | 355.00 | 6.8747 | 301.46 | 39.88 |
| 13.0590 | 0.0857 | 15.77 | 357.00 | 6.7796 | 275.95 | 36.50 |
| 14.2525 | 0.0768 | 25.61 | 363.00 | 6.2144 | 338.26 | 44.75 |

TABLE 8-continued

XRPD peak table for IRDye 800 BK, pattern 7 (example #2).

| Pos. [°2Th.] ± 0.2 | FWHM [°2Th.] | Area [cts*°2Th.] | Backgr. [cts] | d-spacing [Å] | Height [cts] | Rel. Int. [%] |
|---|---|---|---|---|---|---|
| 14.7903 | 0.1023 | 31.95 | 359.00 | 5.9896 | 316.50 | 41.87 |
| 15.8886 | 0.2047 | 25.58 | 366.92 | 5.5780 | 126.71 | 16.76 |
| 16.3661 | 0.0768 | 19.14 | 368.00 | 5.4163 | 252.79 | 33.44 |
| 16.6528 | 0.0768 | 32.09 | 367.00 | 5.3237 | 423.90 | 56.07 |
| 17.4262 | 0.1023 | 25.26 | 353.00 | 5.0891 | 250.24 | 33.10 |
| 18.4166 | 0.2577 | 34.36 | 373.39 | 4.8176 | 200.00 | 26.46 |
| 19.0409 | 0.1023 | 34.06 | 394.41 | 4.6611 | 337.43 | 44.63 |
| 19.1703 | 0.0768 | 25.89 | 398.00 | 4.6299 | 341.96 | 45.23 |
| 19.5584 | 0.1279 | 45.43 | 405.00 | 4.5389 | 360.01 | 47.62 |
| 19.8202 | 0.1023 | 35.86 | 408.00 | 4.4795 | 355.21 | 46.99 |
| 20.1452 | 0.1535 | 12.67 | 409.00 | 4.4080 | 83.67 | 11.07 |
| 20.6292 | 0.1279 | 41.30 | 406.00 | 4.3056 | 327.27 | 43.29 |
| 21.0630 | 0.1279 | 95.39 | 399.00 | 4.2179 | 755.97 | 100.00 |
| 21.9260 | 0.1279 | 25.59 | 374.66 | 4.0538 | 202.83 | 26.83 |
| 22.4269 | 0.3070 | 47.21 | 353.13 | 3.9644 | 155.87 | 20.62 |
| 23.3628 | 0.1279 | 27.00 | 331.00 | 3.8077 | 213.99 | 28.31 |
| 25.0858 | 0.3070 | 28.03 | 339.00 | 3.5499 | 92.57 | 12.25 |
| 26.1965 | 0.1279 | 30.58 | 317.16 | 3.4019 | 242.31 | 32.05 |

IRDye 800 BK, Pattern 7—Example 3

TABLE 9

XRPD peak table for IRDye 800 BK, pattern 7 (example 3).

| Pos. [°2Th.] ± 0.2 | FWHM [°2Th.] | Area [cts*°2Th.] | Backgr. [cts] | d-spacing [Å] | Height [cts] | Rel. Int. [%] |
|---|---|---|---|---|---|---|
| 4.7525 | 0.0768 | 39.03 | 327.70 | 18.5942 | 515.52 | 51.43 |
| 6.4133 | 0.0768 | 22.31 | 242.94 | 13.7820 | 294.72 | 29.40 |
| 9.5423 | 0.1535 | 42.35 | 200.75 | 9.2687 | 279.70 | 27.90 |
| 9.7287 | 0.0768 | 33.98 | 206.00 | 9.0916 | 448.75 | 44.77 |
| 11.2915 | 0.0768 | 18.20 | 269.00 | 7.8365 | 240.34 | 23.98 |
| 11.5662 | 0.0895 | 40.67 | 277.00 | 7.6510 | 460.45 | 45.94 |
| 12.8685 | 0.0768 | 45.47 | 318.61 | 6.8795 | 600.60 | 59.92 |
| 13.8466 | 0.1535 | 24.34 | 330.00 | 6.3957 | 160.72 | 16.03 |
| 14.7928 | 0.1151 | 55.64 | 316.00 | 5.9886 | 489.88 | 48.87 |
| 16.3690 | 0.0640 | 27.01 | 336.00 | 5.4154 | 428.13 | 42.71 |
| 16.6409 | 0.0768 | 41.40 | 338.00 | 5.3275 | 546.75 | 54.55 |
| 16.8349 | 0.0573 | 13.84 | 338.00 | 5.2665 | 361.91 | 36.10 |
| 17.4402 | 0.0768 | 36.77 | 330.00 | 5.0851 | 485.59 | 48.44 |
| 18.4146 | 0.1279 | 19.96 | 328.00 | 4.8181 | 158.18 | 15.78 |
| 19.1745 | 0.0895 | 29.34 | 351.00 | 4.6289 | 332.11 | 33.13 |
| 19.5641 | 0.1279 | 35.70 | 357.00 | 4.5376 | 282.91 | 28.22 |
| 19.8677 | 0.1279 | 43.14 | 360.00 | 4.4689 | 341.85 | 34.10 |
| 20.1675 | 0.1535 | 33.91 | 361.00 | 4.4032 | 223.96 | 22.34 |
| 20.6219 | 0.1535 | 40.62 | 359.00 | 4.3072 | 268.27 | 26.76 |
| 21.0557 | 0.1023 | 101.19 | 355.00 | 4.2194 | 1002.39 | 100.00 |
| 21.4262 | 0.1151 | 66.85 | 347.00 | 4.1472 | 588.65 | 58.72 |
| 21.9224 | 0.0768 | 34.66 | 333.00 | 4.0545 | 457.78 | 45.67 |
| 22.1607 | 0.1854 | 41.32 | 324.00 | 4.0114 | 334.31 | 33.35 |
| 22.4158 | 0.1791 | 54.80 | 312.98 | 3.9664 | 310.21 | 30.95 |
| 23.3843 | 0.1535 | 28.14 | 291.00 | 3.8042 | 185.84 | 18.54 |
| 26.2037 | 0.1279 | 29.43 | 299.00 | 3.4010 | 233.21 | 23.27 |
| 27.7506 | 0.1279 | 17.27 | 249.61 | 3.2148 | 136.86 | 13.65 |
| 29.8914 | 0.1535 | 16.48 | 222.00 | 2.9892 | 108.87 | 10.86 |
| 30.4268 | 0.1535 | 15.73 | 212.00 | 2.9379 | 103.87 | 10.36 |

IRDye 800 BK, Pattern 8

TABLE 10

XRPD peak table for IRDye 800 BK, pattern 8.

| Pos. [°2Th.] ± 0.2 | FWHM [°2Th.] | Area [cts*°2Th.] | Backgr. [cts] | d-spacing [Å] | Height [cts] | Rel. Int. [%] |
|---|---|---|---|---|---|---|
| 3.7959 | 0.0512 | 46.12 | 444.28 | 23.2772 | 913.75 | 55.23 |
| 4.0476 | 0.0512 | 17.83 | 422.92 | 21.8304 | 353.17 | 21.35 |
| 4.2031 | 0.0640 | 24.76 | 408.96 | 21.0233 | 392.43 | 23.72 |
| 8.3543 | 0.0640 | 18.38 | 248.64 | 10.5839 | 291.33 | 17.61 |
| 9.4760 | 0.0768 | 51.73 | 241.00 | 9.3334 | 683.19 | 41.30 |
| 12.6117 | 0.2580 | 62.19 | 302.00 | 7.0190 | 361.55 | 21.85 |
| 12.7040 | 0.0640 | 39.49 | 303.95 | 6.9682 | 625.96 | 37.84 |
| 12.8225 | 0.0640 | 27.60 | 305.00 | 6.9041 | 437.41 | 26.44 |
| 16.0096 | 0.0768 | 29.58 | 293.00 | 5.5361 | 390.73 | 23.62 |
| 16.3054 | 0.0768 | 21.29 | 291.00 | 5.4364 | 281.24 | 17.00 |
| 19.0394 | 0.1151 | 129.81 | 255.00 | 4.6614 | 1143.02 | 69.09 |
| 19.2256 | 0.0768 | 46.70 | 257.00 | 4.6167 | 616.85 | 37.29 |
| 19.5420 | 0.0640 | 33.96 | 260.00 | 4.5427 | 538.25 | 32.54 |
| 19.8052 | 0.0895 | 39.52 | 259.80 | 4.4829 | 447.44 | 27.05 |
| 20.6831 | 0.1279 | 208.75 | 256.00 | 4.2945 | 1654.33 | 100.00 |
| 20.9865 | 0.1279 | 172.16 | 253.00 | 4.2331 | 1364.34 | 82.47 |
| 22.4302 | 0.0477 | 6.03 | 243.12 | 3.9638 | 189.38 | 11.45 |
| 22.6488 | 0.0100 | 1.96 | 244.00 | 3.9261 | 294.12 | 17.78 |
| 22.8361 | 0.1279 | 52.29 | 243.00 | 3.8943 | 414.39 | 25.05 |

IRDye 800 BK, Pattern 9

TABLE 11

XRPD peak table for IRDye 800 BK, pattern 9.

| Pos. [°2Th.] ± 0.2 | FWHM [°2Th.] | Area [cts*°2Th.] | Backgr. [cts] | d-spacing [Å] | Height [cts] | Rel. Int. [%] |
|---|---|---|---|---|---|---|
| 4.7369 | 0.1173 | 15.35 | 344.89 | 18.6551 | 196.23 | 16.11 |
| 5.0962 | 0.0895 | 19.59 | 327.26 | 17.3409 | 221.80 | 18.21 |
| 5.5045 | 0.0512 | 16.85 | 303.85 | 16.0555 | 333.90 | 27.41 |
| 5.7533 | 0.1023 | 13.62 | 288.00 | 15.3616 | 134.90 | 11.07 |
| 8.5415 | 0.1023 | 13.74 | 209.00 | 10.3524 | 136.11 | 11.17 |
| 9.5196 | 0.1535 | 22.76 | 195.00 | 9.2908 | 150.33 | 12.34 |
| 10.3423 | 0.1279 | 40.83 | 201.00 | 8.5535 | 323.57 | 26.56 |
| 11.0176 | 0.1023 | 15.89 | 215.00 | 8.0307 | 157.36 | 12.92 |
| 11.5803 | 0.0512 | 15.75 | 227.00 | 7.6417 | 312.00 | 25.61 |
| 12.5222 | 0.0768 | 12.47 | 248.97 | 7.0690 | 164.74 | 13.52 |
| 12.7176 | 0.0768 | 28.09 | 255.00 | 6.9608 | 371.07 | 30.46 |
| 12.8879 | 0.0768 | 16.67 | 259.00 | 6.8692 | 220.14 | 18.07 |
| 13.5487 | 0.0768 | 30.59 | 268.00 | 6.5356 | 404.01 | 33.16 |
| 13.7110 | 0.0512 | 27.41 | 268.00 | 6.4586 | 543.03 | 44.58 |
| 13.9016 | 0.0768 | 41.83 | 268.92 | 6.3705 | 552.46 | 45.35 |
| 15.2962 | 0.0895 | 81.50 | 282.00 | 5.7927 | 922.70 | 75.74 |
| 16.0437 | 0.1151 | 77.39 | 293.00 | 5.5244 | 681.41 | 55.94 |
| 16.5958 | 0.0640 | 25.06 | 289.00 | 5.3419 | 397.18 | 32.60 |
| 17.1330 | 0.1023 | 59.52 | 278.00 | 5.1756 | 589.57 | 48.40 |
| 17.3437 | 0.0768 | 25.18 | 272.15 | 5.1132 | 332.61 | 27.30 |
| 17.7460 | 0.0895 | 19.23 | 258.00 | 4.9982 | 217.70 | 17.87 |
| 19.1836 | 0.1151 | 64.59 | 256.00 | 4.6267 | 568.76 | 46.69 |
| 19.6740 | 0.1151 | 53.12 | 264.00 | 4.5125 | 467.76 | 38.40 |
| 19.9658 | 0.0512 | 20.67 | 266.00 | 4.4472 | 409.45 | 33.61 |
| 20.6988 | 0.1023 | 122.97 | 271.00 | 4.2913 | 1218.18 | 100.00 |
| 21.2504 | 0.1023 | 59.24 | 270.00 | 4.1812 | 586.82 | 48.17 |
| 21.9056 | 0.0768 | 39.83 | 260.00 | 4.0576 | 526.05 | 43.18 |
| 23.0183 | 0.0895 | 45.17 | 254.37 | 3.8639 | 511.39 | 41.98 |
| 23.4439 | 0.1535 | 25.17 | 264.00 | 3.7947 | 166.22 | 13.64 |
| 24.8681 | 0.1791 | 22.79 | 269.35 | 3.5805 | 129.01 | 10.59 |
| 25.8542 | 0.1535 | 28.23 | 277.00 | 3.4461 | 186.43 | 15.30 |
| 26.7482 | 0.1535 | 23.42 | 279.00 | 3.3329 | 154.65 | 12.70 |
| 27.3808 | 0.1279 | 37.36 | 265.00 | 3.2574 | 296.03 | 24.30 |
| 27.8578 | 0.1279 | 27.71 | 249.37 | 3.2027 | 219.60 | 18.03 |
| 28.6271 | 0.1279 | 25.40 | 246.00 | 3.1183 | 201.28 | 16.52 |
| 32.0149 | 0.2047 | 27.41 | 230.00 | 2.7957 | 135.75 | 11.14 |

IRDye 800 BK, Pattern 10

TABLE 12

XRPD peak table for IRDye 800 BK, pattern 10.

| Pos. [°2Th.]± 0.2 | FWHM [°2Th.] | Area [cts*°2Th.] | Backgr. [cts] | d-spacing [Å] | Height [cts] | Rel. Int. [%] |
|---|---|---|---|---|---|---|
| 4.4888 | 0.0768 | 12.17 | 397.00 | 19.6857 | 160.73 | 5.55 |
| 9.4943 | 0.0768 | 16.84 | 279.00 | 9.3155 | 222.43 | 7.67 |
| 10.2475 | 0.0895 | 33.59 | 280.00 | 8.6325 | 380.25 | 13.12 |
| 12.6585 | 0.0640 | 30.23 | 290.00 | 6.9932 | 479.05 | 16.53 |
| 12.8795 | 0.0512 | 15.42 | 292.00 | 6.8737 | 305.51 | 10.54 |
| 13.4903 | 0.0768 | 71.60 | 297.00 | 6.5638 | 945.69 | 32.63 |
| 14.3086 | 0.0768 | 36.35 | 304.00 | 6.1902 | 480.15 | 16.57 |
| 14.4438 | 0.0512 | 14.88 | 305.00 | 6.1326 | 294.76 | 10.17 |
| 16.0250 | 0.0768 | 70.94 | 360.00 | 5.5308 | 937.00 | 32.33 |
| 16.3818 | 0.0512 | 22.63 | 375.00 | 5.4112 | 448.35 | 15.47 |
| 16.8301 | 0.0895 | 48.68 | 393.00 | 5.2680 | 551.10 | 19.02 |
| 18.0204 | 0.1279 | 45.28 | 435.00 | 4.9227 | 358.80 | 12.38 |
| 19.0628 | 0.1023 | 127.86 | 462.00 | 4.6557 | 1266.56 | 43.70 |
| 19.2792 | 0.0895 | 126.24 | 466.00 | 4.6040 | 1429.20 | 49.31 |
| 19.7252 | 0.0640 | 42.41 | 473.00 | 4.5009 | 672.15 | 23.19 |
| 20.5520 | 0.1023 | 292.57 | 479.00 | 4.3216 | 2898.18 | 100.00 |
| 21.0470 | 0.1023 | 232.60 | 480.00 | 4.2211 | 2304.13 | 79.50 |
| 21.2625 | 0.1023 | 49.53 | 479.00 | 4.1788 | 490.64 | 16.93 |
| 21.5370 | 0.0895 | 113.95 | 478.00 | 4.1262 | 1290.07 | 44.51 |
| 21.9648 | 0.1279 | 20.94 | 474.00 | 4.0468 | 165.91 | 5.72 |
| 22.4527 | 0.0768 | 20.06 | 469.00 | 3.9599 | 264.98 | 9.14 |
| 22.6815 | 0.0895 | 64.92 | 465.55 | 3.9205 | 734.95 | 25.36 |
| 23.7543 | 0.1023 | 25.49 | 448.00 | 3.7458 | 252.52 | 8.71 |
| 26.0477 | 0.1535 | 22.06 | 406.60 | 3.4210 | 145.65 | 5.03 |
| 27.5804 | 0.1535 | 17.87 | 390.00 | 3.2342 | 118.04 | 4.07 |
| 28.7431 | 0.1279 | 38.89 | 380.00 | 3.1060 | 308.20 | 10.63 |
| 33.0752 | 0.4093 | 35.96 | 325.00 | 2.7084 | 89.05 | 3.07 |
| 23.3912 | 0.1535 | 39.87 | 392.00 | 3.8031 | 263.29 | 11.99 |
| 24.8986 | 0.0900 | 5.81 | 365.00 | 3.5762 | 96.78 | 4.41 |
| 25.6787 | 0.3070 | 24.76 | 349.00 | 3.4693 | 81.75 | 3.72 |
| 26.5685 | 0.3070 | 36.61 | 330.00 | 3.3551 | 120.89 | 5.50 |
| 27.4754 | 0.2047 | 28.38 | 318.78 | 3.2464 | 140.55 | 6.40 |
| 28.6492 | 0.2047 | 40.54 | 310.49 | 3.1160 | 200.77 | 9.14 |
| 29.8906 | 0.0900 | 6.02 | 300.00 | 2.9893 | 100.34 | 4.57 |
| 32.0444 | 0.1535 | 27.28 | 278.00 | 2.7932 | 180.15 | 8.20 |

IRDye 800 BK, Pattern 11

TABLE 13

XRPD peak table for IRDye 800 BK, pattern 11.

| Pos. [°2Th.] ± 0.2 | FWHM [°2Th.] | Area [cts*°2Th.] | Backgr. [cts] | d-spacing [Å] | Height [cts] | Rel. Int. [%] |
|---|---|---|---|---|---|---|
| 4.2468 | 0.1535 | 40.88 | 553.60 | 20.8070 | 270.00 | 15.71 |
| 5.3149 | 0.0512 | 47.49 | 496.43 | 16.6276 | 940.77 | 54.75 |
| 6.0027 | 0.0512 | 29.30 | 458.53 | 14.7239 | 580.50 | 33.79 |
| 9.5925 | 0.1535 | 53.98 | 352.00 | 9.2204 | 356.50 | 20.75 |
| 10.6191 | 0.1279 | 68.31 | 354.00 | 8.3311 | 541.32 | 31.51 |
| 10.9673 | 0.1535 | 35.66 | 356.00 | 8.0675 | 235.53 | 13.71 |
| 11.4281 | 0.1023 | 26.57 | 357.00 | 7.7432 | 263.16 | 15.32 |
| 11.9996 | 0.0895 | 54.06 | 358.00 | 7.3756 | 612.05 | 35.62 |
| 12.9117 | 0.1151 | 72.65 | 358.00 | 6.8566 | 639.74 | 37.23 |
| 14.2428 | 0.1407 | 133.03 | 354.00 | 6.2187 | 958.41 | 55.78 |
| 15.2161 | 0.4093 | 52.91 | 357.20 | 5.8230 | 131.02 | 7.63 |
| 15.9725 | 0.2047 | 108.14 | 365.00 | 5.5489 | 535.60 | 31.17 |
| 16.4322 | 0.1023 | 47.22 | 369.00 | 5.3947 | 467.73 | 27.22 |
| 16.7868 | 0.1279 | 42.91 | 373.00 | 5.2815 | 340.09 | 19.79 |
| 17.4036 | 0.1279 | 67.07 | 387.00 | 5.0957 | 531.55 | 30.94 |
| 18.6999 | 0.1535 | 51.94 | 419.00 | 4.7453 | 343.01 | 19.96 |
| 19.2027 | 0.1279 | 66.87 | 427.00 | 4.6221 | 529.94 | 30.84 |
| 19.6564 | 0.1535 | 61.51 | 432.00 | 4.5165 | 406.19 | 23.64 |
| 20.2085 | 0.1023 | 32.94 | 436.00 | 4.3943 | 326.31 | 18.99 |
| 20.7567 | 0.1279 | 119.49 | 436.00 | 4.2795 | 946.91 | 55.11 |
| 21.2861 | 0.1535 | 260.17 | 433.00 | 4.1742 | 1718.18 | 100.00 |
| 21.8633 | 0.2047 | 46.52 | 428.00 | 4.0653 | 230.41 | 13.41 |
| 22.6653 | 0.2047 | 45.95 | 415.00 | 3.9233 | 227.57 | 13.24 |
| 23.4725 | 0.1791 | 75.59 | 399.00 | 3.7901 | 427.86 | 24.90 |

TABLE 13-continued

XRPD peak table for IRDye 800 BK, pattern 11.

| Pos. [°2Th.] ± 0.2 | FWHM [°2Th.] | Area [cts*°2Th.] | Backgr. [cts] | d-spacing [Å] | Height [cts] | Rel. Int. [%] |
|---|---|---|---|---|---|---|
| 23.9892 | 0.2047 | 37.22 | 386.95 | 3.7097 | 184.36 | 10.73 |
| 24.9923 | 0.1535 | 46.34 | 360.79 | 3.5630 | 306.03 | 17.81 |
| 26.5063 | 0.1535 | 60.12 | 327.00 | 3.3628 | 397.02 | 23.11 |
| 32.0733 | 0.5117 | 49.95 | 257.10 | 2.7907 | 98.96 | 5.76 |
| 33.3376 | 0.3070 | 22.62 | 241.00 | 2.6877 | 74.68 | 4.35 |

IRDye 800 BK, Pattern 12

TABLE 14

XRPD peak table for IRDye 800 BK, pattern 12.

| Pos. [°2Th.] ± 0.2 | FWHM [°2Th.] | Area [cts*°2Th.] | Backgr. [cts] | d-spacing [Å] | Height [cts] | Rel. Int. [%] |
|---|---|---|---|---|---|---|
| 4.1778 | 0.0512 | 300.08 | 536.90 | 21.1505 | 5945.12 | 96.49 |
| 4.7486 | 0.0900 | 5.58 | 517.00 | 18.6095 | 92.99 | 1.51 |
| 8.6746 | 0.0900 | 9.53 | 435.00 | 10.1939 | 158.87 | 2.58 |
| 9.7531 | 0.0768 | 20.71 | 427.00 | 9.0688 | 273.56 | 4.44 |
| 11.2876 | 0.0900 | 7.01 | 432.00 | 7.8392 | 116.88 | 1.90 |
| 12.5423 | 0.0512 | 45.54 | 463.00 | 7.0577 | 902.28 | 14.64 |
| 12.8866 | 0.0900 | 16.70 | 479.00 | 6.8699 | 278.32 | 4.52 |
| 13.0770 | 0.0895 | 77.91 | 488.00 | 6.7703 | 882.01 | 14.31 |
| 13.7174 | 0.0768 | 42.89 | 517.91 | 6.4556 | 566.50 | 9.19 |
| 14.3498 | 0.0768 | 43.14 | 547.56 | 6.1725 | 569.78 | 9.25 |
| 15.6166 | 0.0900 | 7.52 | 632.00 | 5.6746 | 125.26 | 2.03 |
| 16.1781 | 0.0768 | 114.97 | 679.19 | 5.4788 | 1518.53 | 24.64 |
| 16.9088 | 0.0768 | 69.11 | 737.40 | 5.2437 | 912.84 | 14.81 |
| 17.4098 | 0.1015 | 45.86 | 774.94 | 5.0939 | 677.91 | 11.00 |
| 18.2385 | 0.1149 | 43.55 | 827.69 | 4.8643 | 568.33 | 9.22 |
| 18.9911 | 0.0768 | 165.95 | 863.00 | 4.6732 | 2191.89 | 35.57 |
| 19.2905 | 0.0895 | 141.03 | 873.61 | 4.6013 | 1596.66 | 25.91 |
| 19.5898 | 0.0895 | 161.13 | 881.00 | 4.5317 | 1824.17 | 29.61 |
| 20.1370 | 0.0895 | 109.07 | 889.00 | 4.4098 | 1234.75 | 20.04 |
| 20.5000 | 0.1023 | 279.87 | 890.00 | 4.3325 | 2772.34 | 44.99 |
| 21.0467 | 0.1023 | 622.01 | 884.00 | 4.2212 | 6161.62 | 100.00 |
| 21.5523 | 0.1023 | 80.65 | 872.00 | 4.1233 | 798.90 | 12.97 |
| 21.7719 | 0.2022 | 120.49 | 865.00 | 4.0822 | 893.61 | 14.50 |
| 22.4342 | 0.0895 | 77.71 | 838.00 | 3.9631 | 879.78 | 14.28 |
| 22.9433 | 0.1023 | 63.28 | 812.41 | 3.8763 | 626.81 | 10.17 |
| 23.8261 | 0.1535 | 34.23 | 762.50 | 3.7347 | 226.05 | 3.67 |
| 25.4988 | 0.1535 | 31.17 | 694.00 | 3.4934 | 205.86 | 3.34 |
| 27.7321 | 0.1535 | 31.14 | 656.04 | 3.2169 | 205.64 | 3.34 |
| 28.7467 | 0.1023 | 44.82 | 639.00 | 3.1056 | 444.01 | 7.21 |
| 32.9203 | 0.2047 | 40.69 | 529.00 | 2.7208 | 201.54 | 3.27 |

IRDye 800 BK, Pattern 13

TABLE 15

XRPD peak table for IRDye 800 BK, pattern 13.

| Pos. [°2Th.] ± 0.2 | FWHM [°2Th.] | Area [cts*°2Th.] | Backgr. [cts] | d-spacing [Å] | Height [cts] | Rel. Int. [%] |
|---|---|---|---|---|---|---|
| 4.2203 | 0.0640 | 40.44 | 400.00 | 20.9374 | 640.96 | 30.24 |
| 5.1537 | 0.0768 | 38.20 | 387.00 | 17.1475 | 504.55 | 23.80 |
| 5.3163 | 0.0768 | 30.67 | 384.00 | 16.6232 | 405.09 | 19.11 |
| 5.9742 | 0.0768 | 60.08 | 372.00 | 14.7941 | 793.56 | 37.44 |
| 7.2872 | 0.1791 | 49.65 | 341.72 | 12.1312 | 281.07 | 13.26 |
| 8.4097 | 0.1023 | 23.36 | 312.37 | 10.5143 | 231.37 | 10.91 |
| 9.5180 | 0.1023 | 34.25 | 326.00 | 9.2924 | 339.32 | 16.01 |
| 10.3043 | 0.1279 | 37.61 | 344.37 | 8.5850 | 298.06 | 14.06 |
| 10.6500 | 0.1535 | 42.26 | 352.00 | 8.3070 | 279.08 | 13.17 |
| 11.9583 | 0.0895 | 120.50 | 377.59 | 7.4010 | 1364.22 | 64.36 |
| 12.6457 | 0.1023 | 48.60 | 388.47 | 7.0002 | 481.39 | 22.71 |
| 12.9094 | 0.1023 | 89.83 | 392.00 | 6.8578 | 889.82 | 41.98 |
| 13.2458 | 0.1023 | 39.27 | 397.00 | 6.6844 | 389.07 | 18.35 |
| 13.8413 | 0.1279 | 37.11 | 404.44 | 6.3981 | 294.12 | 13.87 |

TABLE 15-continued

XRPD peak table for IRDye 800 BK, pattern 13.

| Pos. [°2Th.] ± 0.2 | FWHM [°2Th.] | Area [cts*°2Th.] | Backgr. [cts] | d-spacing [Å] | Height [cts] | Rel. Int. [%] |
|---|---|---|---|---|---|---|
| 14.2685 | 0.1535 | 42.17 | 409.30 | 6.2075 | 278.46 | 13.14 |
| 15.3744 | 0.1151 | 184.26 | 443.37 | 5.7634 | 1622.44 | 76.54 |
| 16.0496 | 0.1535 | 55.63 | 470.00 | 5.5224 | 367.39 | 17.33 |
| 16.3726 | 0.1279 | 58.80 | 482.15 | 5.4142 | 465.97 | 21.98 |
| 16.7000 | 0.1535 | 57.86 | 494.00 | 5.3088 | 382.12 | 18.03 |
| 17.4196 | 0.1535 | 52.36 | 517.70 | 5.0910 | 345.80 | 16.31 |
| 17.8996 | 0.1791 | 85.91 | 531.61 | 4.9556 | 486.30 | 22.94 |
| 18.3234 | 0.2047 | 55.85 | 542.22 | 4.8419 | 276.63 | 13.05 |
| 19.3205 | 0.2047 | 197.00 | 563.00 | 4.5942 | 975.72 | 46.03 |
| 19.8607 | 0.1535 | 84.94 | 571.00 | 4.4705 | 560.92 | 26.46 |
| 20.8110 | 0.1407 | 294.24 | 578.00 | 4.2684 | 2119.82 | 100.00 |
| 21.1317 | 0.1023 | 110.47 | 579.00 | 4.2044 | 1094.30 | 51.62 |
| 21.3228 | 0.1535 | 153.66 | 579.00 | 4.1671 | 1014.74 | 47.87 |
| 22.5150 | 0.1279 | 96.19 | 575.00 | 3.9491 | 762.32 | 35.96 |
| 23.4166 | 0.2047 | 46.79 | 567.00 | 3.7991 | 231.76 | 10.93 |
| 24.3324 | 0.1535 | 65.96 | 554.00 | 3.6581 | 435.58 | 20.55 |
| 27.1625 | 0.3070 | 52.30 | 490.85 | 3.2830 | 172.70 | 8.15 |
| 27.9429 | 0.4093 | 42.98 | 468.82 | 3.1931 | 106.43 | 5.02 |
| 28.9722 | 0.3070 | 40.10 | 444.00 | 3.0820 | 132.41 | 6.25 |

The patterns in the present example are obtainable using the crystallization methods in Example 1 in accordance with the following. The top row in the table are the number of hours the solid polymorph dried before collecting XRPD data.

|  | 4 hrs | 24 hrs | 48 hrs | 72 hrs | 80 hrs | 90 hrs | 100 hrs | 140 hrs |
|---|---|---|---|---|---|---|---|---|
| Crystallization 1 |  | Pattern 13 | Pattern 13 |  |  |  |  | Pattern 13 |
| Crystallization 2 |  | Pattern 11 | Pattern 1 |  |  |  |  | Pattern 1 |
| Crystallization 3 |  |  |  | Pattern 13 |  | Pattern 13 | Pattern 13 |  |
| Crystallization 4 |  |  |  |  |  |  | Pattern 11 |  |
| Crystallization 5 |  |  | Pattern 11 |  |  | Pattern 13 |  |  |
| Crystallization 6 |  | Pattern 11 |  |  | Pattern 11 |  |  |  |
| Crystallization 7 |  | Pattern 9 |  |  | Pattern 11 |  |  |  |
| Crystallization 8 |  |  | Pattern 11 |  | Pattern 13 |  |  |  |
| Crystallization 9 | Pattern 1 |  |  |  |  |  |  |  |

Example 3: Mouse Urine

It is believed that the renal system is the primary elimination route for a compound of Formula I. In this example, mice receive a compound of Formula I or indocyanine green (ICG) by injection. Urine is obtained from mice that received: neither of the compound of Formula I or ICG (control), a compound of Formula I, or mice that receive ICG. The urine is extracted with an acetonitrile:methanol mix and imaged on an Odyssey CLx imager (LI-COR Biosciences).

No fluorescent signal is seen for the control and ICG. ICG is eliminated by the liver so no signal is expected. There is a fluorescent signal for the compound of Formula I.

Example 4: Excised Organ Evaluation

Fluorescent signal intensities of various organs is examined at 24 hrs and 72 hrs for compounds of Formula I. Organs examined included: heart (Ht), lungs (Ln), kidney (Kd), liver (Lv), spleen (Spl), intestine (Int), brain (Br), and muscle (Ms). At 24 hrs, there remains some signal in the liver and kidney, but by 72 hrs the signal is diminished substantially.

Example 5: Elimination Routes in Mice

This example the dyes tested are 800 CW and a compound of Formula I. In this study a total of 12 nude mice (3 per treatment group) are injected with either (1) no probe (control group); (2) 800 CW; or (3) a compound of Formula I. The two probes (800 CW-1091.1 g/mole), and 800 Formula I—1113.14 g/mole) are dissolved in PBS. A spot test of the two probes is performed to detect the fluorescent signal when diluted to the injection dose of 1 nmole/100 μl. The fluorescence of 800 CW is slightly higher than that of a compound of Formula I.

The mice receive 1 nmole of dye by tail vein injection. The mice are imaged serially over 24 hours after IV injection: 5 minutes, 1 hour, 2 hours, 4 hours, 6 hours and 24 hours after injection. All the data are normalized to the same LUT. A control mouse (no probe) is used as a reference (no signal control). Imaging is performed using the Pearl® Trilogy Imaging System (LI-COR®).

The mice are sacrificed and their organs and tissue (i.e., liver, kidney, lungs, spleen and muscle) are harvested. The organs are imaged to detect fluorescence. Kidneys and liver have a detectable signal in the animals treated with the probes. No muscle or lung tissue is visible in the treatments except for the 800 CW treatment. 800 CW and a compound of Formula I are excreted renally.

The organs are imaged under three LUT scales; each being progressively smaller in the signal range covered. The lower levels of each progressive scale is expanded to cover the full red to blue color range. Very little signal remains in any of the target organs such as liver, kidney, lungs and muscle. Similar signal intensities are found in the kidney for 800 CW and a compound of Formula I. In the liver, a compound of Formula I has a higher signal compared to 800 CW. The results show that the inventive compound has a longer retention time in the liver compared to 800 CW.

This example shows that the clearance is rapid from the whole body to the biliary system with a very short retention time in the liver and is also rapid excretion into the intestines.

Example 6: Ureter Visualization During a Hysterectomy or Colectomy

The pharmaceutical formulation of Formula I is dissolved in a vial (25 mg) with 5 mL of saline (0.9% sodium chloride) and is administered to a patient via a bolus injection at the concentration of 5 mg/mL, 15 minutes prior to the surgery. The medical device for this procedure is the PINPOINT Endoscopic Fluorescence Imaging System (Novadaq, Mississauga, Ontario, Canada). At any point during the procedure, when the surgeon needs to identify the ureter, the device's mode is switched to the near-infrared detection imaging, and the surgeon visualizes the ureter via the monitor or display of the medical device. This identification of the ureter is visualized on the monitor as an overlay image, in which the surgeon can simultaneously locate the ureter with white light imaging.

Example 7: Biliary Duct Visualization During a Cholecystectomy

The pharmaceutical formulation of a compound of Formula I is dissolved in a vial (25 mg) with 5 mL of saline (0.9% sodium chloride) and is administered to a patient via a bolus injection at the concentration of 5 mg/mL, 15 minutes prior to the surgery starting. The medical device for this procedure is the da Vinci Firefly Surgical System (Intuitive Surgical, Sunnyvale Calif.). During the procedure, when the surgeon needs to identify the biliary duct, the device's mode is switched to the near-infrared detection imaging, and the surgeon identifies the biliary duct via the monitor or display of the medical device by switching between the white light image and the near-infrared image as needed.

Example 8: Comparison of X-Ray Powder Diffraction (XRPD) Patterns

Figure 16:
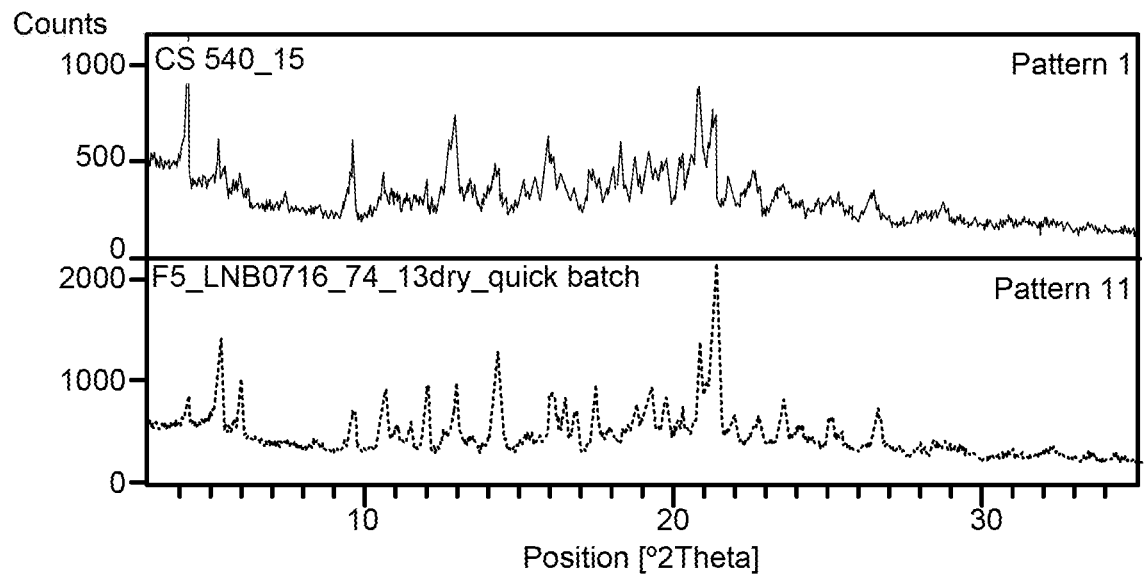
FIG. 16 shows an X-ray powder diffraction (XRPD) pattern comparison of a solid form of Formula I which is form A-1, Pattern 1, which appears above form A-11, Pattern 11.
Figure 17:
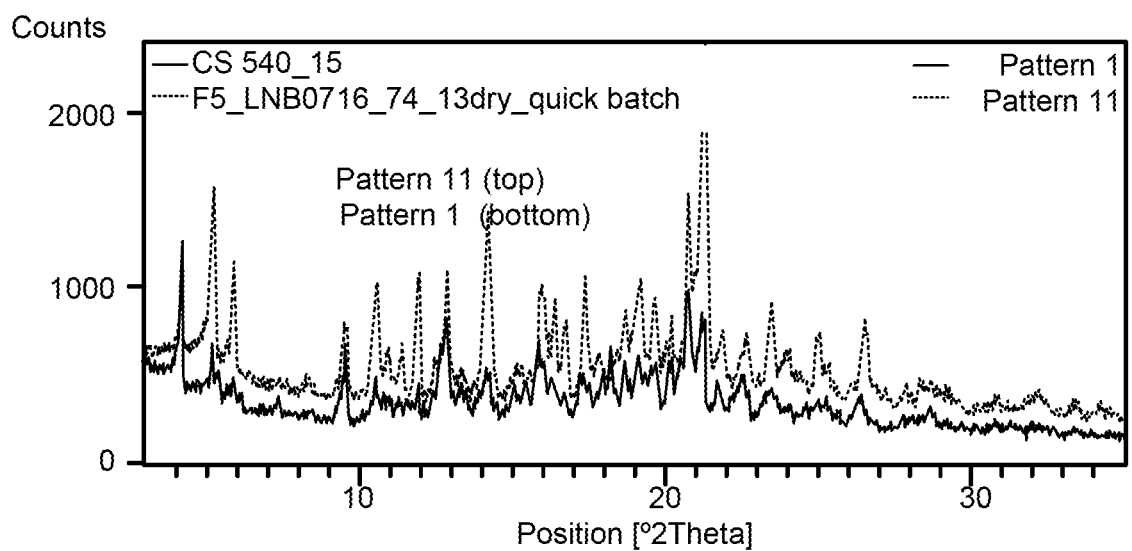
FIG. 17 shows an X-ray powder diffraction (XRPD) pattern comparison of a solid form of Formula I which is form A-1, Pattern 11, which appears above form A-1, Pattern 1.
Figure 18A:
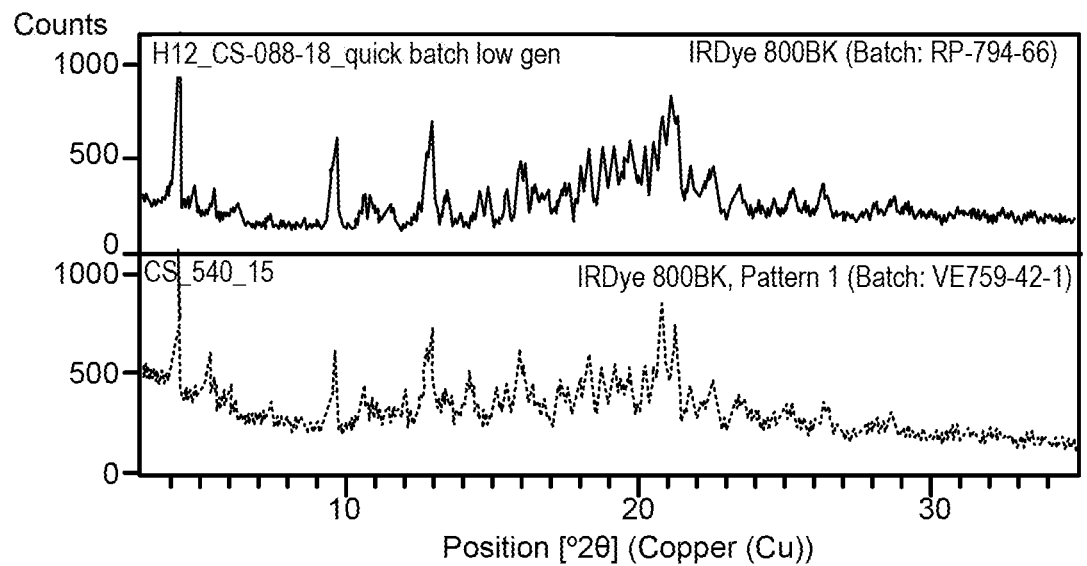
FIG. 18A compares Pattern 1 in FIG. 1A with Pattern 1 in FIG. 1B.
Figure 18B:
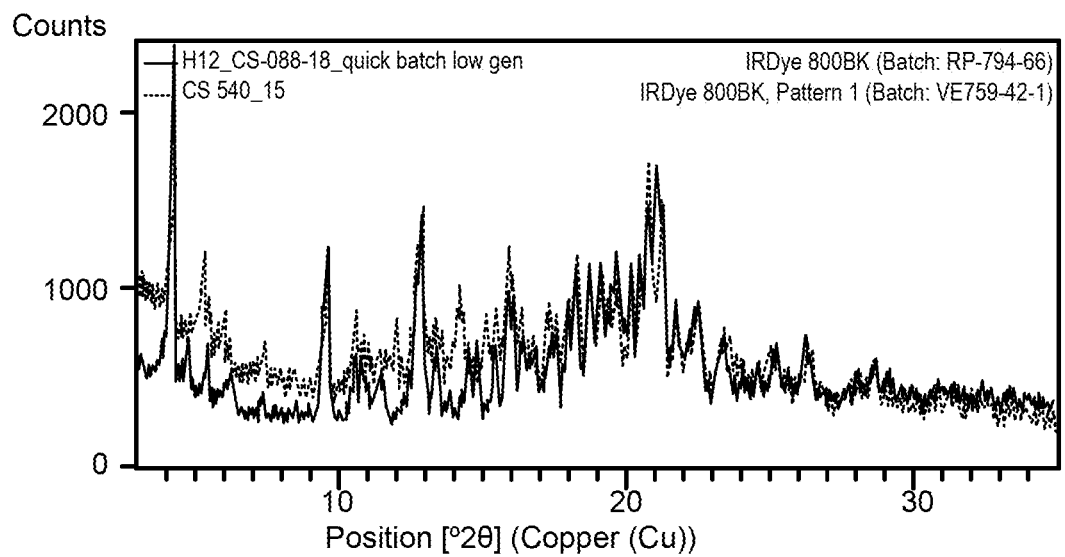
FIG. 18B compares Pattern 1 in FIG. 1A with Pattern 1 in FIG. 1B.

XRPD analysis was carried out on a Panalytical X'pert pro, scanning the samples between 3 and 35° 2θ for pattern 1 and pattern 11. The results are shown in FIG. 16. FIG. 17 is an overlay of pattern 11 above pattern 1.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A solid polymorphic form of Formula I:

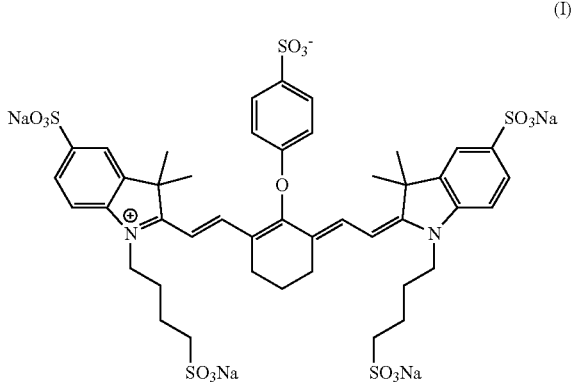

(I)

wherein the solid polymorphic form is a member selected from the group consisting of A-2, A-3, A-4, A-5, A-6, A-7, A-8, A-9, A-10, A-12 and A-13, wherein Form A-2 is characterized by an X-ray powder diffraction (XRPD) pattern comprising peaks at 21.0201, 21.3092, 21.9298 and 16.4226 degrees 2θ (±0.2 degrees 2 θ);

Form A-3 is characterized by an X-ray powder diffraction (XRPD) pattern comprising peaks at 5.4582, 8.9758, 15.5042, 18.0678 degrees 2θ (±0.2 degrees 2 θ);

Form A-4 is characterized by an X-ray powder diffraction (XRPD) pattern comprising peaks at 4.6095, 6.1473, 11.9990, 12.4243, 16.4064, and 20.4115 degrees 2θ (±0.2 degrees 2 θ), Form A-5 is characterized by an X-ray powder diffraction (XRPD) pattern comprising peaks at 5.0928, 5.3751, 7.1146, and 19.2858 degrees 2θ (±0.2 degrees 2 θ);

Form A-6 is characterized by an X-ray powder diffraction (XRPD) pattern comprising peaks at 11.8430, 4.7214, 5.6359, 10.7093, 17.1609 and 18.1502 degrees 2θ (±0.2 degrees 2 θ);

Form A-7 is characterized by an X-ray powder diffraction (XRPD) pattern comprising peaks at 21.1726, 21.0470, 11.9862, and 5.9858 degrees 2θ (±0.2 degrees 2 θ);

Form A-8 is characterized by an X-ray powder diffraction (XRPD) pattern comprising peaks 20.6831, 20.9865, and 19.0394 degrees 2θ (±0.2 degrees 2 θ);

Form A-9 is characterized by an X-ray powder diffraction (XRPD) pattern comprising peaks 20.6988, 15.2962, 13.9016, and 13.7110 degrees 2θ (±0.2 degrees 2 θ);

Form A-10 is characterized by an X-ray powder diffraction (XRPD) pattern comprising peaks 20.5520, 21.0470, 21.5370 and 19.0628 degrees 2θ (±0.2 degrees 2 θ);

Form A-12 is characterized by an X-ray powder diffraction (XRPD) pattern comprising peaks 21.0467, 20.5000 and 4.1778 degrees 2θ (±0.2 degrees 2 θ); and Form A-13 is characterized by an X-ray powder diffraction (XRPD) pattern comprising peaks 20.8110, 11.9583 and 19.3205 degrees 2θ (±0.2 degrees 2 θ).

2. A method for kidney ureter imaging, the method comprising:
providing to a subject a composition comprising a diagnostic effective amount of a polymorph of Formula I according to claim 1;
administering said composition one or more times selected from the group consisting of before a procedure, during a procedure, after a procedure and combinations thereof,
exposing tissue of the subject's renal system to electromagnetic radiation; and
detecting fluorescence radiation from the compound.

3. The method of claim 2, wherein the administering is conducted intravenously.

4. The method of claim 2, wherein the pharmaceutically acceptable cation is selected from the group consisting of potassium or sodium.

5. The method of claim 2, wherein the composition comprises a pharmaceutically acceptable carrier selected from the group consisting of physiological sterile saline solution, sterile water solution, pyrogen-free water solution, isotonic or 0.5N saline solution, and phosphate buffer solution.

6. The method of claim 2, wherein the administering is conducted at a diagnostic effective amount of the compound ranging between approximately 0.01 μg/kg and approximately 3000.0 μg/kg.

7. The method of claim 2, further comprising measuring a fluorescence intensity of the administered compound remaining at the tissue of the subject's renal system at a time period after administering.

8. The method of claim 2, wherein the measured fluorescence intensity of the administered compound is comparable to background fluorescence approximately 24 hours after administering.

9. The method of claim 2, wherein the procedure is selected from the group consisting of a laparoscopic procedure, a robotic procedure, a robotic laparoscopic procedure, and an open procedure.

10. The method of claim 7, wherein the measured fluorescence intensity of the administered compound is higher in the kidney as compared to a measured fluorescence intensity of the administered compound in one or more of the spleen, intestine, heart, lungs, muscle, or combinations thereof approximately up to six hours after administering.

11. A pharmaceutical composition comprising a diagnostic imaging amount of a polymorph of Formula I,

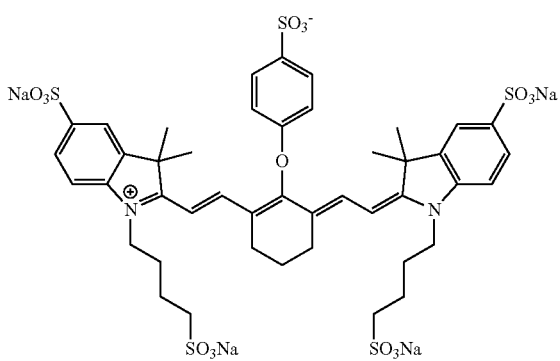

wherein the polymorphic form is a member selected from the group consisting of A-2, A-3, A-4, A-5, A-6, A-7, A-8, A-9, A-10, A-12 and A-13, wherein
Form A-2 is characterized by an X-ray powder diffraction (XRPD) pattern comprising peaks at 21.0201, 21.3092, 21.9298 and 16.4226 degrees 2θ (±0.2 degrees 2 θ);
Form A-3 is characterized by an X-ray powder diffraction (XRPD) pattern comprising peaks at 5.4582, 8.9758, 15.5042, 18.0678 degrees 2θ (±0.2 degrees 2 θ);
Form A-4 is characterized by an X-ray powder diffraction (XRPD) pattern comprising peaks at 4.6095, 6.1473, 11.9990, 12.4243, 16.4064, and 20.4115 degrees 2θ (±0.2 degrees 2 θ),
Form A-5 is characterized by an X-ray powder diffraction (XRPD) pattern comprising peaks at 5.0928, 5.3751, 7.1146, and 19.2858 degrees 2θ (±0.2 degrees 2 θ);
Form A-6 is characterized by an X-ray powder diffraction (XRPD) pattern comprising peaks at 11.8430, 4.7214, 5.6359, 10.7093, 17.1609 and 18.1502 degrees 2θ (±0.2 degrees 2 θ);
Form A-7 is characterized by an X-ray powder diffraction (XRPD) pattern comprising peaks at 21.1726, 21.0470, 11.9862, and 5.9858 degrees 2θ (±0.2 degrees 2 θ);
Form A-8 is characterized by an X-ray powder diffraction (XRPD) pattern comprising peaks 20.6831, 20.9865, and 19.0394 degrees 2θ (±0.2 degrees 2 θ);
Form A-9 is characterized by an X-ray powder diffraction (XRPD) pattern comprising peaks 20.6988, 15.2962, 13.9016, and 13.7110 degrees 2θ (±0.2 degrees 2 θ);
Form A-10 is characterized by an X-ray powder diffraction (XRPD) pattern comprising peaks 20.5520, 21.0470, 21.5370 and 19.0628 degrees 2θ (±0.2 degrees 2 θ);
Form A-12 is characterized by an X-ray powder diffraction (XRPD) pattern comprising peaks 21.0467, 20.5000 and 4.1778 degrees 2θ (±0.2 degrees 2 θ);
Form A-13 is characterized by an X-ray powder diffraction (XRPD) pattern comprising peaks 20.8110, 11.9583 and 19.3205 degrees 2θ (±0.2 degrees 2 θ);
and a pharmaceutically acceptable carrier.

12. The pharmaceutical composition of claim 11, wherein the pharmaceutically acceptable carrier comprises saline.

13. The pharmaceutical composition of claim 11, wherein the polymorph is a polymorph selected from the group consisting of A-2, A-3, and A-4.

14. The pharmaceutical composition of claim 11, wherein the formulation comprises reconstitution of a lyophilized cake having a sugar or a sugar alcohol and an organic acid.

15. The pharmaceutical composition of claim 14, wherein the acid is a member selected from the group consisting of citric acid, malic acid, tartaric acid, lactic acid, formic acid, ascorbic acid, fumaric acid, gluconic acid, succinic acid, maleic acid, adipic acid, and any mixture thereof.

16. The pharmaceutical composition of claim 14, wherein the sugar or the sugar alcohol is a member selected from the group consisting of erythritol, tagatose, sucrose, fructose, glucose, sorbitol, mannitol, maltitol, xylitol, glycyrrhizin, malitol, maltose, lactose, xylose, arabinose, isomalt, lactitol, trehalulose, ribose, and any mixture thereof.

17. A kit comprising the pharmaceutical composition of claim 11, and an instruction manual.

* * * * *